United States Patent
Asano

(10) Patent No.: US 7,300,524 B2
(45) Date of Patent: Nov. 27, 2007

(54) SUBSTRATE CLEANING METHOD

(75) Inventor: Toru Asano, Kyoto (JP)

(73) Assignee: Dainippon Screen Mfg. Co., Ltd. (JP)

( * ) Notice: Subject to any disclaimer, the term of this patent is extended or adjusted under 35 U.S.C. 154(b) by 27 days.

(21) Appl. No.: 11/235,008

(22) Filed: Sep. 21, 2005

(65) Prior Publication Data

US 2006/0016462 A1 Jan. 26, 2006

Related U.S. Application Data

(62) Division of application No. 10/210,577, filed on Jul. 30, 2002, now abandoned.

(30) Foreign Application Priority Data

| Aug. 8, 2001 | (JP) | ............................. 2001-240677 |
| Aug. 8, 2001 | (JP) | ............................. 2001-240678 |

(51) Int. Cl.
*B08B 7/04* (2006.01)

(52) U.S. Cl. ............................. 134/18; 134/1.3; 134/6; 134/33; 134/37

(58) Field of Classification Search .................. 134/18, 134/33, 34, 37, 1.3, 32
See application file for complete search history.

(56) References Cited

U.S. PATENT DOCUMENTS 5,701,627 A 12/1997 Matsumura et al.
5,756,155 A * 5/1998 Tzeng et al. ................. 427/294
5,865,901 A 2/1999 Yin et al.
6,059,891 A * 5/2000 Kubota et al. ................. 134/18
2002/0189758 A1 12/2002 Shiga et al.

FOREIGN PATENT DOCUMENTS

| JP | 2000-243796 | 9/2000 |
| JP | 2001-195731 | 7/2001 |

* cited by examiner

*Primary Examiner*—Michael Barr
*Assistant Examiner*—Saeed Chaudhry
(74) *Attorney, Agent, or Firm*—Ostrolenk, Faber, Gerb & Soffen, LLP

(57) ABSTRACT

A substrate cleaning apparatus includes an indexer, a front surface cleaning unit for cleaning the front surface of a substrate, a back surface cleaning unit for cleaning the back surface of the substrate, a particle inspecting unit for detecting a distribution of particles adhering to the substrate, a reversing unit for reversing the substrate, and a transport section having a pair of transport units. Cleaning conditions of the front surface cleaning unit or back surface cleaning unit are varied based on the distribution of particles on the substrate after the substrate is cleaned by the front surface cleaning unit or back surface cleaning unit and inspected by the particle inspecting unit.

5 Claims, 19 Drawing Sheets

F I G. 1
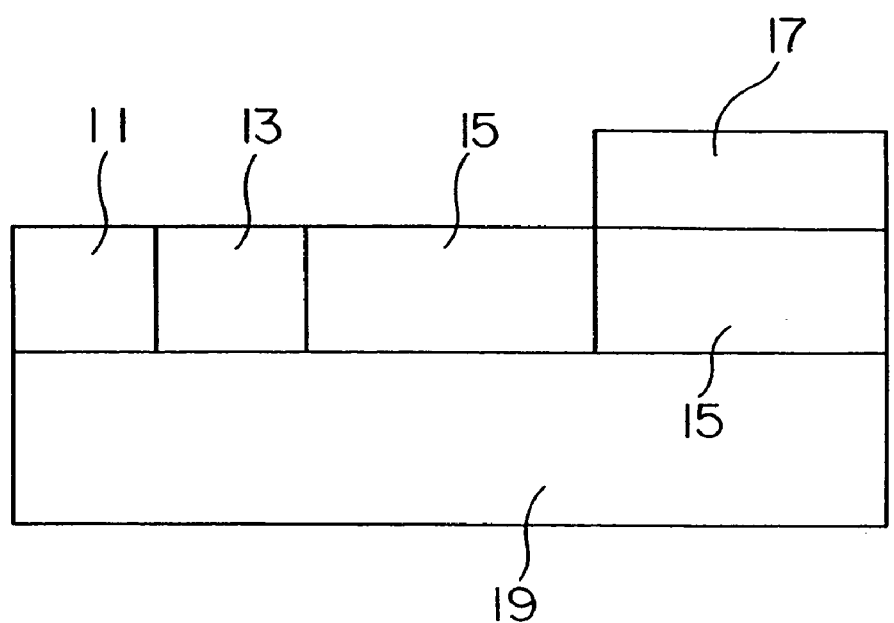

F I G. 1 0
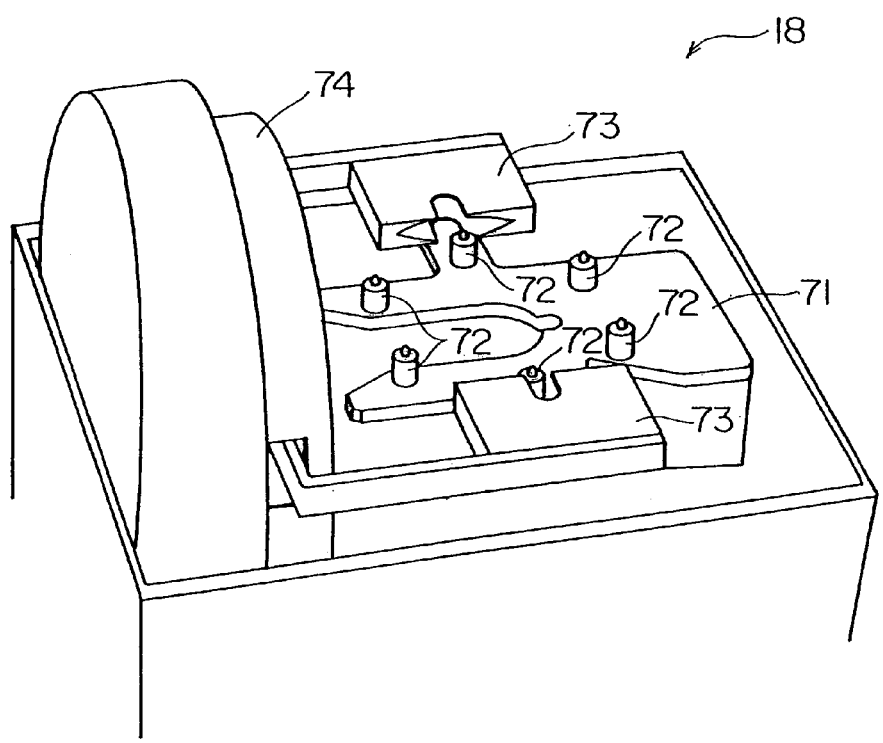

SUBSTRATE CLEANING METHOD

CROSS REFERENCE TO A RELATED APPLICATION

The present application is a Divisional application of Ser. No. 10/210,577 filed Jul. 30, 2002 now abandoned, which application claims the benefit and priority of Japanese Application Ser. No. 2001-240677 filed Aug. 8, 2001 and Japanese Application Ser. No. 2001-240678 filed Aug. 8, 2001, incorporated by reference.

BACKGROUND OF THE INVENTION

1. Field of the Invention

The present invention relates to substrate cleaning apparatus and methods for cleaning substrates such as semiconductor wafers, glass substrates for liquid crystal displays, mask substrates for use in semiconductor manufacturing apparatus, and the like.

2. Description of the Related Art

Such a substrate cleaning apparatus has one of various types of cleaning mechanisms for cleaning substrates. These include a cleaning mechanism for cleaning substrates with a cleaning brush, a cleaning mechanism that supplies substrates with a cleaning solution under high pressure, a cleaning mechanism that supplies substrates with a cleaning solution with ultrasonic vibration applied thereto, and a cleaning mechanism that supplies substrates with a cleaning solution in the form of spray having a liquid-gas mixture.

In the substrate cleaning apparatus having such a cleaning mechanism, the cleaning brush for cleaning substrates or the cleaning solution supply nozzle for supplying a cleaning solution to substrates is variable with time. Such variations bring about variations in the effect of cleaning up particles adhering to surfaces of the substrates. Thus, the substrates could be cleaned only insufficiently.

By way of addressing this problem, it is conceivable to transport each substrate after a cleaning process to a particle inspecting apparatus for detecting a distribution of particles adhering to the substrate, and adjust the varied cleaning mechanism based on the distribution of particles on the substrate detected by the particle inspecting apparatus. Then the cleaning mechanism may effectively clean the substrate.

In this case, however, each cleaned substrate must be transported to the particle inspecting apparatus installed separately from the substrate cleaning apparatus, before detecting a distribution of particles. This poses a problem of requiring an extended time in treating each substrate.

SUMMARY OF THE INVENTION

The object of the present invention, therefore, is to provide a substrate cleaning apparatus and method for cleaning substrates reliably by detecting a distribution of particles on each substrate speedily.

The above object is fulfilled, according to the present invention, by a substrate cleaning apparatus comprising an indexer for receiving a cassette storing a plurality of substrates, a cleaning unit for cleaning a substrate, a particle inspecting unit for detecting a distribution of particles adhering to the substrate, a transport unit for transporting the substrate between the indexer, the cleaning unit and the particle inspecting unit, and a controller for varying substrate cleaning conditions of the cleaning unit based on the distribution of particles adhering to the substrate after the substrate is cleaned by the cleaning unit and inspected by the particle inspecting unit, wherein the substrate is repeatedly cleaned by varying the cleaning conditions of the cleaning unit until the substrate is determined to be clean as a result of inspection by the particle inspecting unit of the distribution of particles on the substrate cleaned by the cleaning unit.

With this substrate cleaning apparatus, a distribution of particles on the substrate cleaned in the cleaning unit is detected and, when the substrate is found not sufficiently clean, the substrate is cleaned again after varying substrate cleaning conditions of the cleaning unit based on the distribution of particles. Thus, the substrate may be cleaned reliably by detecting a distribution of particles on the substrate speedily.

In one preferred embodiment, the cleaning unit includes at least one of a cleaning mechanism for cleaning the substrate with a cleaning brush, a cleaning mechanism that supplies the substrate with a cleaning solution under high pressure, a cleaning mechanism that supplies the substrate with a cleaning solution with ultrasonic vibration applied thereto, and a cleaning mechanism that supplies the substrate with a cleaning solution in form of spray having a liquid-gas mixture.

In another aspect of the invention, a substrate cleaning method is provided for processing substrates by using a substrate cleaning apparatus having an indexer for receiving a cassette storing a plurality of substrates, a cleaning unit for cleaning a substrate, a particle inspecting unit for detecting a distribution of particles adhering to the substrate, and a transport unit for transporting the substrate between the indexer, the cleaning unit and the particle inspecting unit, the method comprising a first cleaning step for cleaning a substrate transported from the cassette to the cleaning unit, a particle detecting step for detecting a distribution of particles on the substrate cleaned by the cleaning unit and transported to the particle inspecting unit, a determining step for determining whether the substrate is clean, based on the distribution of particles detected in the particle detecting step, a cleaning condition varying step for varying substrate cleaning conditions of the cleaning unit based on the distribution of particles detected by the particle inspecting unit when the substrate is determined to be unclean in the determining step, and a second cleaning step for transporting the substrate determined to be unclean after the first cleaning step to the cleaning unit, and cleaning the substrate with the cleaning conditions varied in the cleaning condition varying step.

Other features and advantages of the present invention will be apparent from the following detailed description of the embodiments of the invention.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 1 is a schematic side view of a substrate cleaning apparatus according to the invention;

FIG. 10 is a perspective view showing a principal portion of a reversing unit;

DESCRIPTION OF THE PREFERRED EMBODIMENTS

Figure 2:
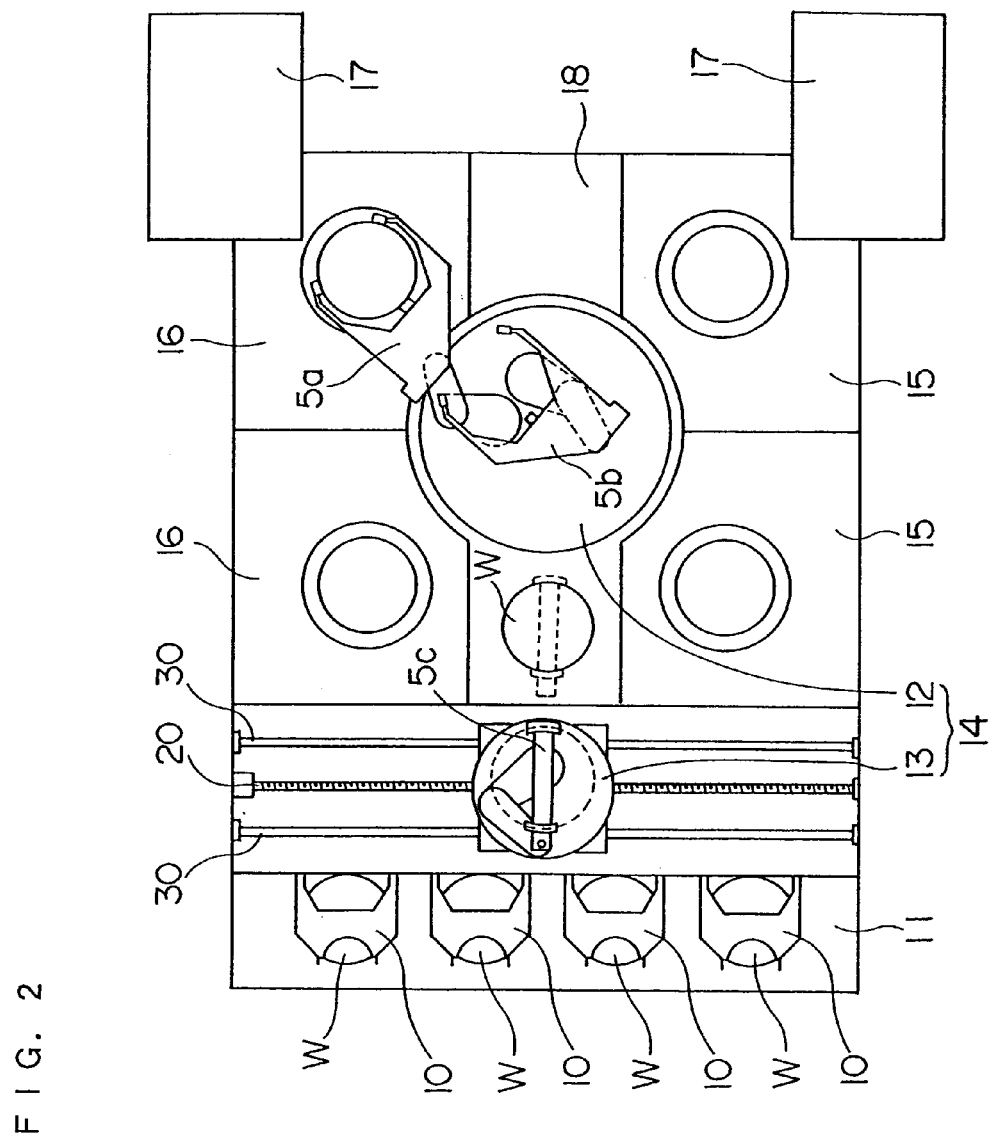
FIG. 2 is a schematic plan view of the substrate cleaning apparatus.

Embodiments of the present invention will be described hereinafter with reference to the drawings. FIG. 1 is a schematic side view of a substrate cleaning apparatus according to the invention. FIG. 2 is a schematic plan view thereof.

This substrate cleaning apparatus includes an indexer 11 for unloading one substrate or wafer W at a time from a cassette 10 storing a plurality of wafers W to be processed and loading processed wafers W back into a cassette 10, a pair of front surface cleaning units 15 for cleaning front surfaces of wafers W, a pair of back surface cleaning units 16 for cleaning back surfaces of wafers W, a pair of particle inspecting units 17 for detecting distributions of particles adhering to wafers W, a reversing unit 18 for reversing each wafer W between a position with the front surface facing up and a position with the back surface facing up, a transport section 14 having a pair of transport units 12 and 13 for transporting wafers W between the indexer 11, front surface cleaning units 15, back surface cleaning units 16, particle inspecting units 17 and reversing unit 18, and a chemical cabinet 19 for accommodating a chemical solution tank, piping and so on.

For expediency of illustration, FIG. 2 shows, as obliquely displaced, the particle inspecting units 17 arranged above one front surface cleaning unit 15 and one back surface cleaning unit 16.

The transport unit 13 disposed alongside the indexer 11 takes wafers W to be processed out of a cassette 10 placed on the indexer 11 and transports the wafers W to the transport unit 12 disposed centrally of the substrate cleaning apparatus, or receives processed wafers W from the transport unit 12 and stores these wafers W in a cassette 10 placed on a support table. The transport unit 12 disposed centrally of the substrate cleaning apparatus accesses the front surface cleaning units 15, back surface cleaning units 16, particle inspecting units 17 and reversing unit 18, and transfers wafers W between these units.

Figure 3:
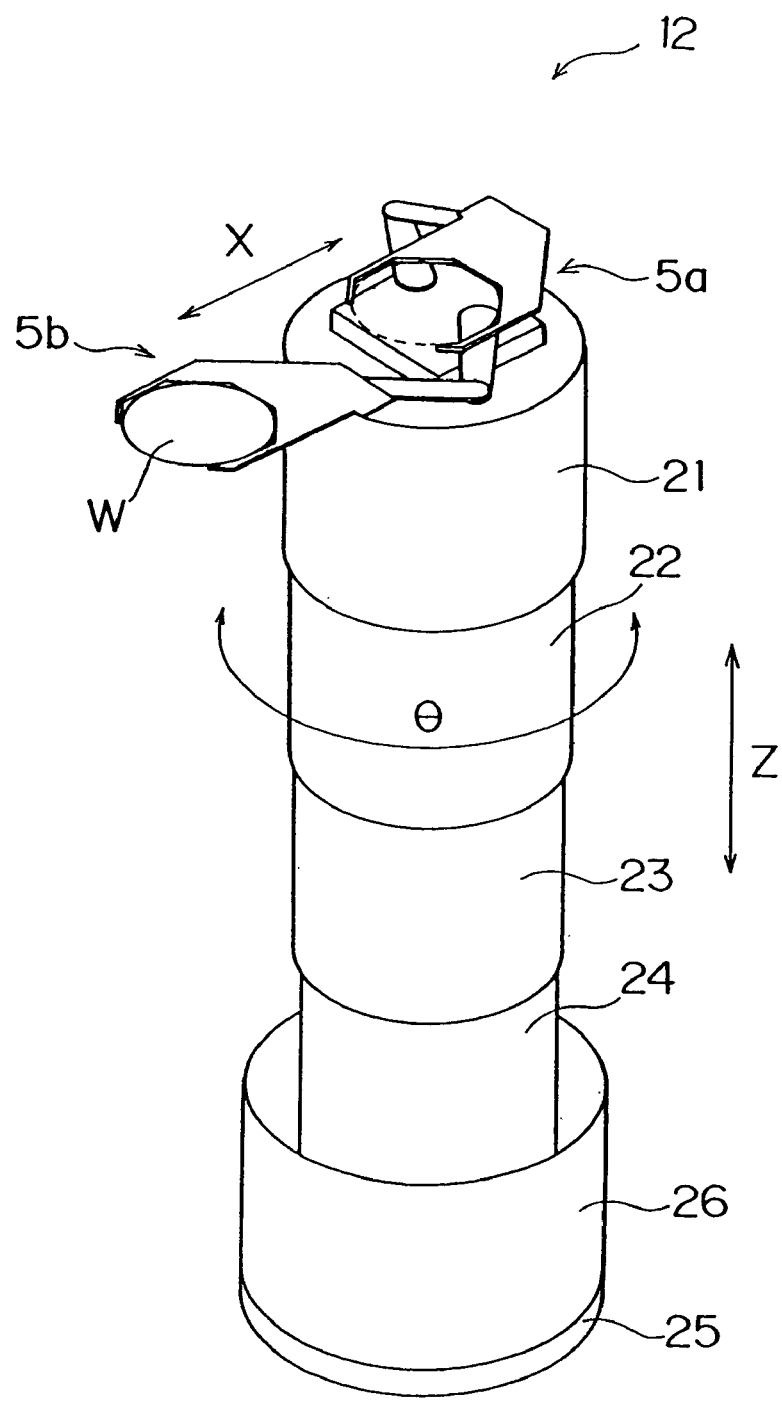
FIG. 3 is a perspective view showing a principal portion of a transport unit.

The transport unit 12 will be described next. FIG. 3 is a perspective view showing a principal portion of the transport unit 12.

This transport unit 12 includes a pair of upper and lower substrate transport arms 5a and 5b for holding and transporting wafers W, horizontal moving mechanisms for moving these substrate transport arms 5a and 5b independently of each other in horizontal directions (X-directions), a telescopic lift mechanism for synchronously moving these substrate transport arms 5a and 5b in vertical directions (Z-directions), and a rotative drive mechanism for synchronously rotating the substrate transport arms 5a and 5b about a vertical axis (in θ-directions).

The above telescopic lift mechanism has a multistage nesting structure of the telescopic type with a cover 24 receivable in a cover 23, the cover 23 in a cover 22 and the cover 22 in a cover 21. When lowering the substrate transport arms 5a and 5b, the cover 24 is moved into the cover 23, the cover 23 into the cover 22, and the cover 22 into the cover 21. When raising the substrate transport arms 5a and 5b, the cover 24 is drawn out of the cover 23, the cover 23 out of the cover 22, and the cover 22 out of the cover 21.

The rotative drive mechanism has a construction for rotating a base 25 of the telescopic lift mechanism in the θ-directions. The base 25 has a cover 26 attached thereto.

Figure 4:
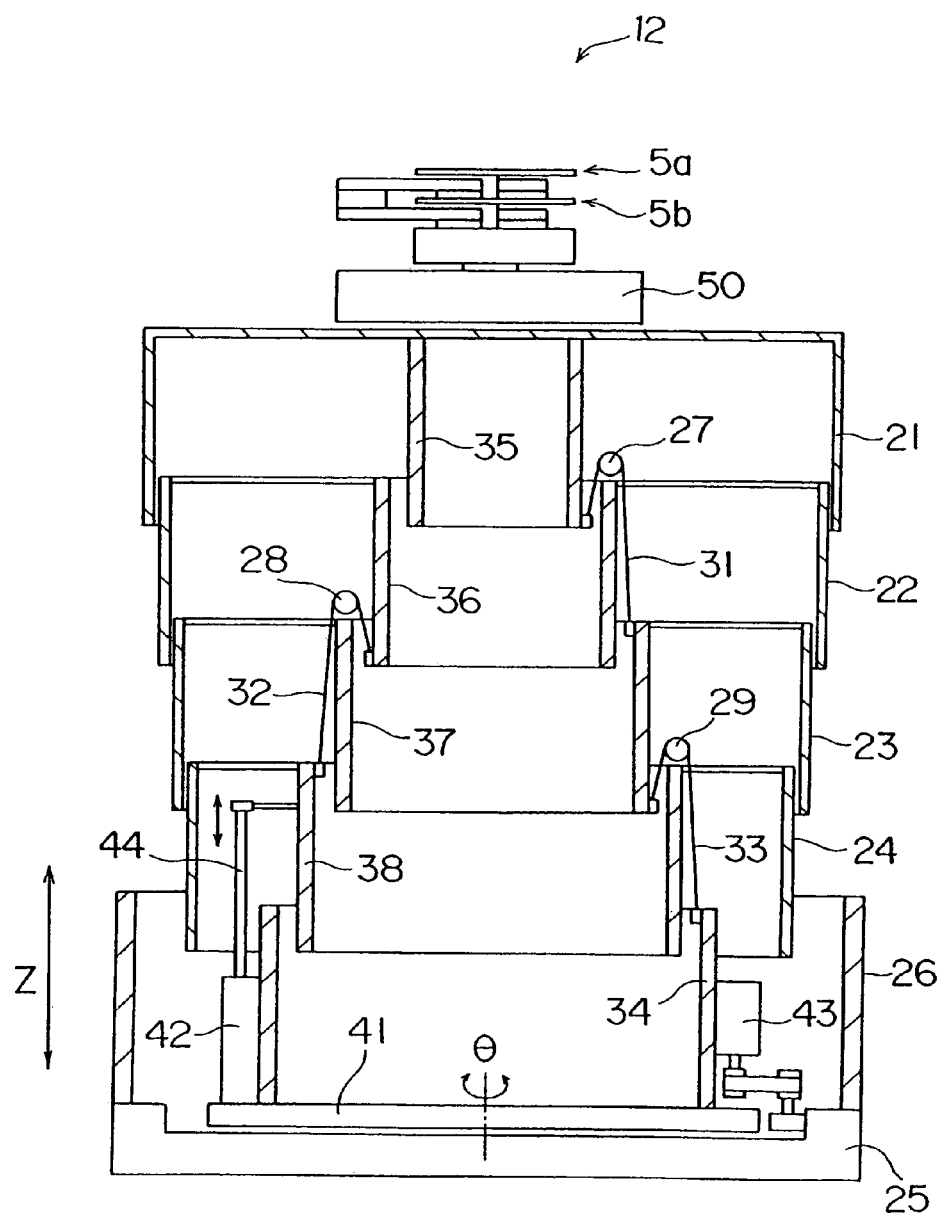
FIG. 4 is a view in vertical section illustrating operation of the transport unit.
Figure 5:
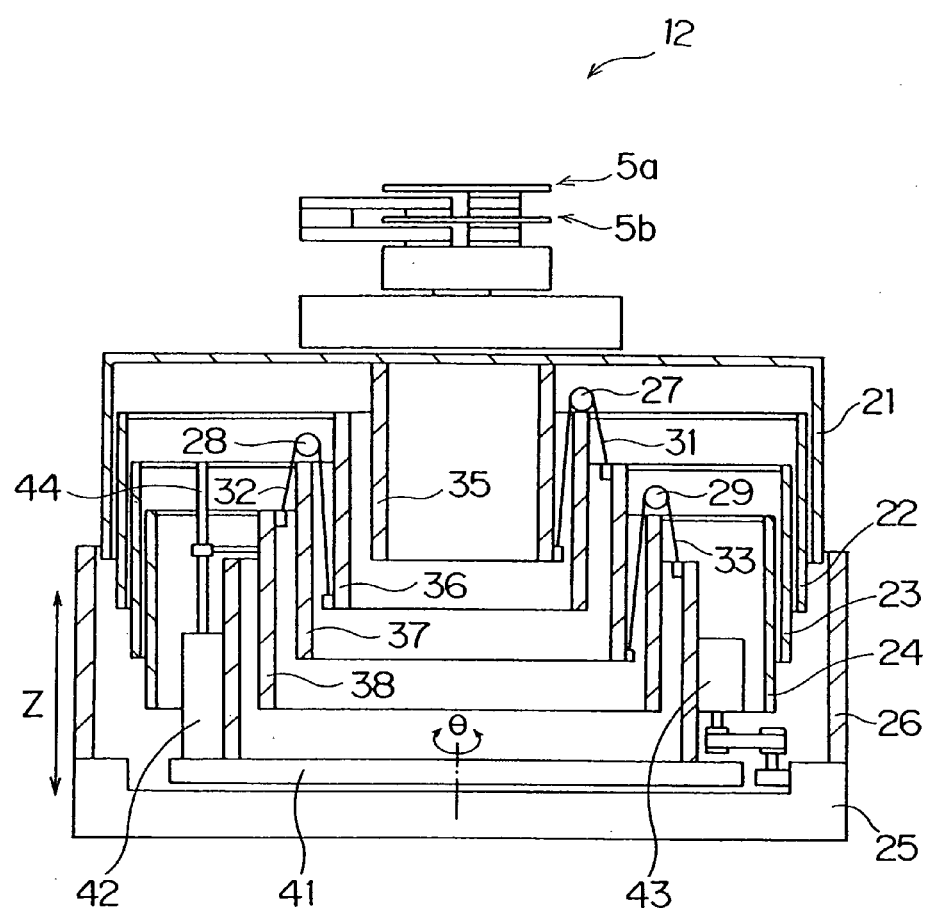
FIG. 5 is another view in vertical section illustrating operation of the transport unit.

FIGS. 4 and 5 are views in vertical section illustrating operation of the transport unit 12. FIG. 4 shows a state of the telescopic lift mechanism being extended. FIG. 5 shows a state of the telescopic lift mechanism being contracted.

The covers 22, 23 and 24 have pulleys 27, 28 and 29 mounted therein, with belts 31, 32 and 33 wound around the pulleys 27, 28 and 29, respectively. The belt 33 is fixed at one end thereof to an upper position of a fixed member 34 disposed in the cover 26, and fixed at the other end to a lower position of a lift member 37 connected to the cover 23. Similarly, the belt 32 is fixed at one end thereof to an upper position of a lift member 38 connected to the cover 24, and fixed at the other end to a lower position of a lift member 36 connected to the cover 22. The belt 31 is fixed at one end thereof to an upper position of a lift member 37 connected to the cover 23, and fixed at the other end to a lower position of a lift member 35 connected to the cover 21.

The lift member 38 is connected to a turntable 41 supporting the fixed member 34, through a ball screw 44 rotatable by a motor 42 mounted on the turntable 41.

With the telescopic lift mechanism having the above construction, when raising the substrate transport arms 5a and 5b, the motor 42 is operated to raise the lift member 38 relative to the turntable 41. As the lift member 38 moves upward, the pulley 29 attached to the lift member 38 also moves upward. Since one end of the belt 33 is fixed to the fixed member 34, the ascent of the pulley 29 causes the belt 33 to pull up the lift member 37. As the lift member 37 moves upward, the pulley 28 attached to the lift member 37 also moves upward, causing the belt 32 to pull up the lift member 36. Similarly, as the lift member 36 moves upward, the pulley 27 attached to the lift member 36 also moves upward, causing the belt 31 to pull up the lift member 35.

When lowering the substrate transport arms 5a and 5b, the motor 42 is operated to lower the lift member 38 relative to the turntable 41. As a result, in an operation reversed from the above operation, the lift members 31, 32 and 33 move downward in an interlocked manner.

In this way, the drive of motor 42 causes the substrate transport arms 5a and 5b to move synchronously up and down.

The turntable 41 supporting the fixed member 34 is rotatable in the θ-directions relative to the base 25. Between the fixed member 34 and base 25 is the rotative drive mechanism having a motor 43. The motor 43 is operable to rotate the fixed member 34 along with the turntable 41 relative to the base 25. The substrate transport arms 5a and 5b may thereby be synchronously rotated about the vertical axis.

Figure 6:
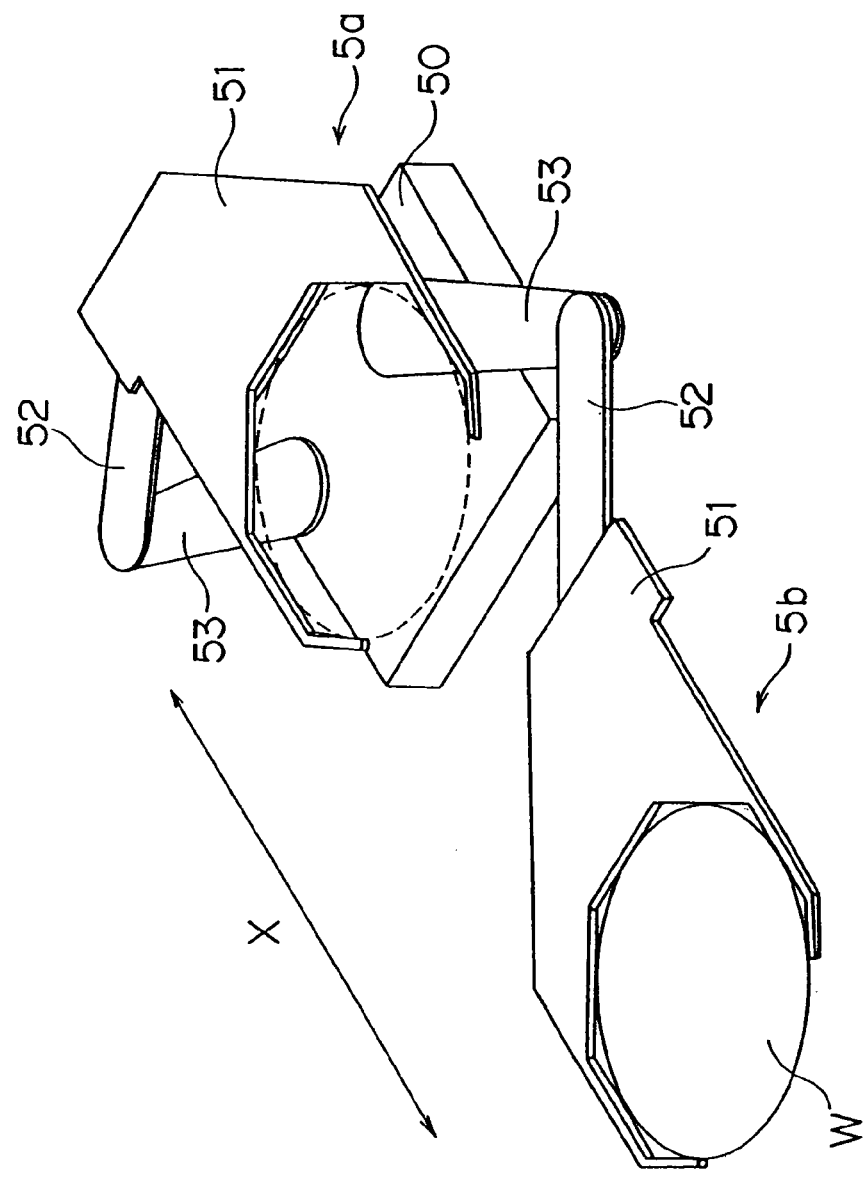
FIG. 6 is a perspective view of substrate transport arms.

The constructions of the substrate transport arms 5a and 5b and the horizontal moving mechanisms for horizontally moving these substrate transport arms 5a and 5b independently of each other will be described next. FIG. 6 is a perspective view of the substrate transport arms 5a and 5b.

Each of these substrate transport arms 5a and 5b includes a substrate holder 51 for holding wafer W above a stage 50, a first connecting member 52 and a second connecting member 53. The first and second connecting members 52 and 53 are flexible to move the substrate holder 51 straight in horizontal directions or X-directions.

Figure 7:
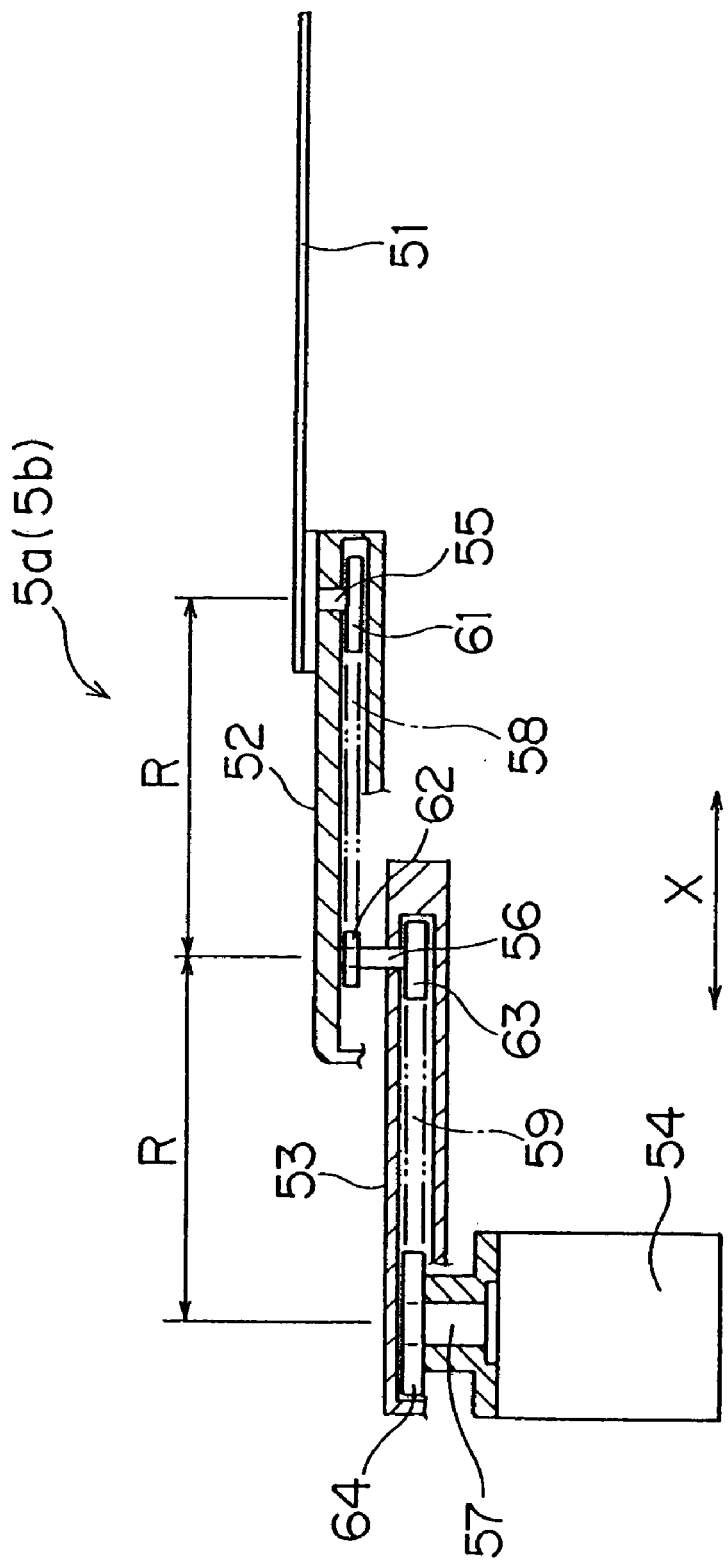
FIG. 7 is a sectional side view showing an internal structure of a substrate transport arm.

FIG. 7 is a sectional side view showing the internal structure of the substrate transport arm 5a. The substrate transport arm 5b has the same structure as this substrate transport arm 5a.

The substrate transport arm 5a includes the substrate holder 51 disposed at a distal end thereof for holding wafer W, the first connecting member 52 for supporting the substrate holder 51 to be pivotable in a horizontal plane, the second connecting member 53 for supporting the first connecting member 52 to be pivotable in a horizontal plane, and the horizontal moving mechanism having a motor 54 for swinging the second connecting member 53 in a horizontal plane.

The substrate holder 51 has a shaft 55 disposed at the proximal end thereof, with a pulley 61 fixed to the shaft 55. The first connecting member 52 has a shaft 56 disposed at the proximal end thereof, with two pulleys 62 and 63 fixed to the shaft 56. Further, the second connecting member 53 has a shaft 57 disposed at the proximal end thereof and connected to the motor 54. A pulley 64 is rotatably mounted on the shaft 57. A synchronous belt 58 extends between the pulley 61 and pulley 62, and a synchronous belt 59 between the pulley 63 and pulley 64.

The diameter of pulley 61 and the diameter of pulley 62 are set to a ratio 2 to 1. The diameter of pulley 63 and the diameter of pulley 64 are set to a ratio 1 to 2. The distance from the shaft 55 to the shaft 56 and the distance from the shaft 56 to the shaft 57 are both set to R.

Figure 8:
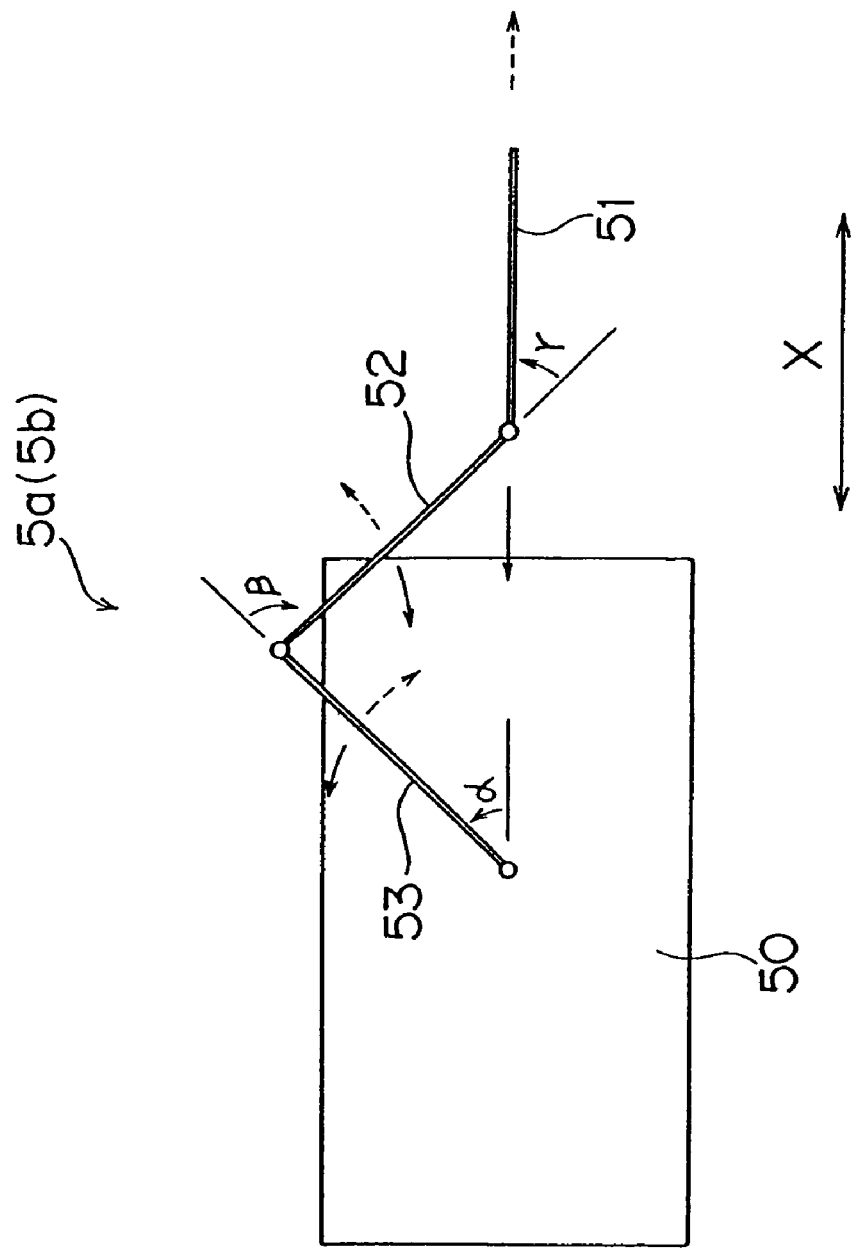
FIG. 8 is an explanatory view conceptually illustrating operation of the substrate transport arm.

FIG. 8 is an explanatory view conceptually illustrating operation of the substrate transport arms 5a and 5b having the above construction.

The drive of motor 54, through the shaft 57, causes the second connecting member 53 to pivot counterclockwise by an angle $\alpha$. As a result, the shaft 56 disposed at the distal end of the second connecting member 53 is driven through the synchronous belt 59 and pulley 63 to rotate clockwise by an angle $\beta=2\alpha$, i.e. twice the rotating angle of the shaft 57. This causes the shaft 55 disposed at the distal end of the first connecting member 52 to move straight in the X-direction shown in FIG. 8.

At this time, the shaft 55 has its rotating angle controlled by the pulleys 61 and 62 and synchronous belt 58. The shaft 55 rotates counterclockwise, relative to the first connecting member 52, by an angle $\gamma=\alpha$ which is half the rotating angle of the shaft 56. Since the first connecting member 52 itself pivots also, the substrate holder 51 moves straight in the X-direction while maintaining the same posture relative to the stage 50.

As described above, the transport unit 12 includes the pair of upper and lower substrate transport arms 5a and 5b for holding and transporting wafers W, the horizontal moving mechanisms for moving these substrate transport arms 5a and 5b independently of each other in horizontal directions, the telescopic lift mechanism for synchronously moving these substrate transport arms 5a and 5b in vertical directions, and the rotative drive mechanism for synchronously rotating the substrate transport arms 5a and 5b about the vertical axis. Thus, the transport unit 12 is constructed for transporting wafers W as held by the substrate holders 51 to selected substrate processing units.

Figure 9:
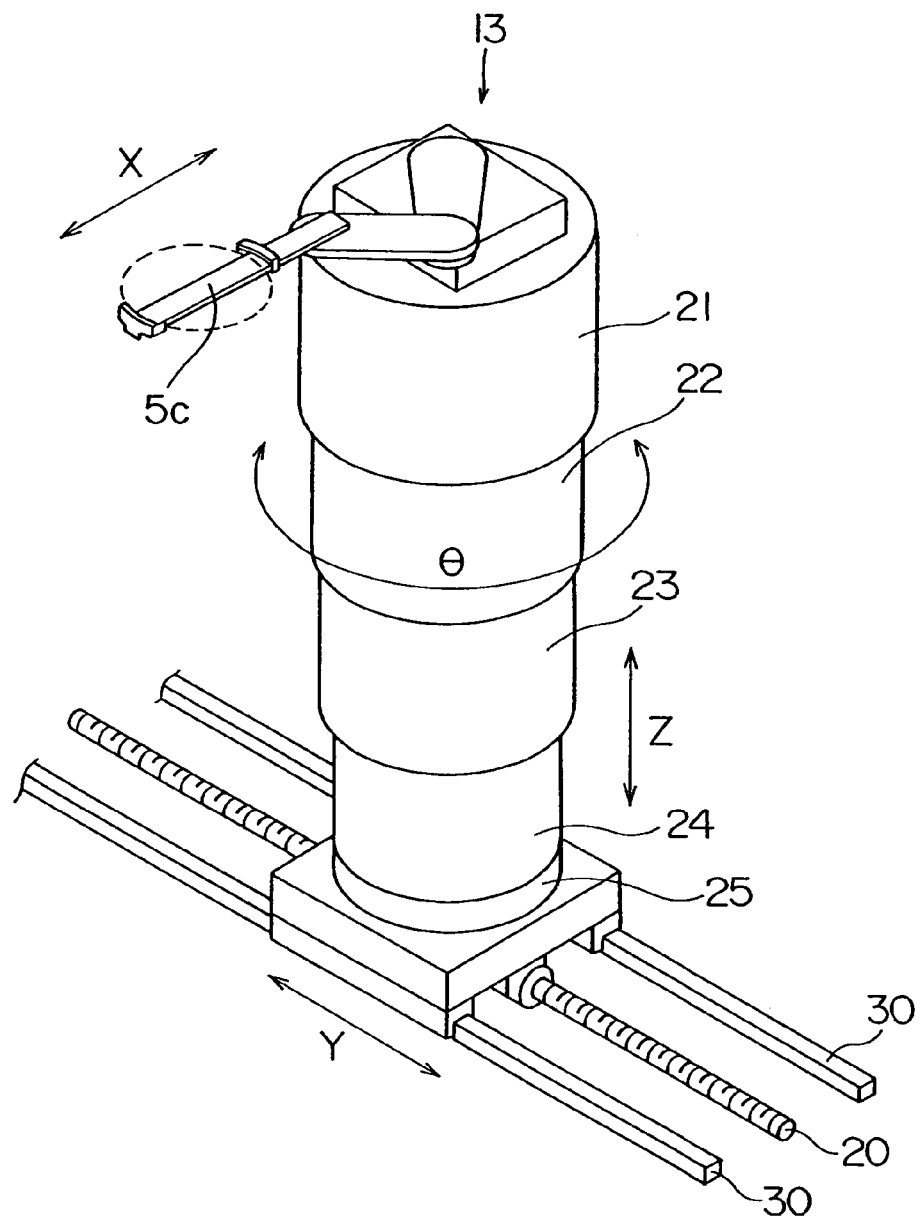
FIG. 9 is a perspective view showing a principal portion of a different transport unit.

The construction of the transport unit 13 will be described next. FIG. 9 is a perspective view showing a principal portion of the transport unit 13.

This transport unit 13 differs from the above transport unit 12 in having a single substrate transport arm 5c as distinct from the pair of upper and lower substrate transport arms 5a and 5b of the transport unit 12. The transport unit 13 is reciprocable by the action of a ball screw 20 rotatable by a motor not shown, along a pair of guide members 30 extending along the indexer 11.

The construction of the reversing unit 18 will be described next. FIG. 10 is a perspective view showing a principal portion of the reversing unit 18.

This reversing unit 18 is operable for turning a wafer W about a horizontal axis to reverse between a position with the front surface facing up and a position with the back surface facing up. The reversing unit 18 has a support table 71 vertically movable by a lift device not shown. The support table 71 has a plurality of substrate support pins 72 arranged thereon for holding the wafer W tight among themselves by contacting only edges of the wafer W. A pair of chucks 73 are arranged above the support table 71 for holding the wafer W held by the substrate support pins 72, tight therebetween by contacting only edges of the wafer W. The pair of chucks 73 are supported by a support member 74 rotatable about a horizontal axis.

When operating the reversing unit 18 to reverse the wafer W, the transport unit 12 places the wafer W on the substrate support pins 72 of the support table 71. The pair of chucks 73 is actuated to hold the wafer W supported on the substrate support pin 72 by contacting opposite edges of the wafer W, and then the support table 71 is lowered. When the support table 71 is fully lowered, the support member 74 is rotated 180 degrees about the horizontal axis along with the pair of chucks 73. As a result, the wafer W rotates 180 degrees to be upside down. Upon completion of the reversal of wafer W, the support table 71 is raised to receive the wafer W on the substrate support pins 72, and the pair of chucks 73 are operated to release the wafer W.

The pair of front surface cleaning units 15 for cleaning the front surfaces of wafers W and the pair of back surface cleaning units 16 for cleaning the back surfaces of wafers W will be described next.

The front surface cleaning units 15 and back surface cleaning units 16 are different only in the shape of spin chucks for supporting wafers W. That is, each front surface cleaning unit 15 uses a spin chuck that supports a wafer W by a central portion of the back surface thereof since the wafer W is cleaned with the front surface facing up. Each back surface cleaning unit 16 uses a spin chuck that supports a wafer W by edges thereof since the wafer W is cleaned with the back surface facing up. In other respects, the front surface cleaning units 15 and back surface cleaning units 16 have the same construction. Thus, the back surface cleaning units 16 will be described hereinafter, omitting description of the front surface cleaning units 15.

The front surface cleaning units 15 and back surface cleaning units 16 may use various types of cleaning mechanisms for cleaning wafers W, such as a cleaning mechanism for cleaning wafers W with a cleaning brush, a cleaning mechanism that supplies wafers W with a cleaning solution under high pressure, a cleaning mechanism that supplies wafers W with a cleaning solution with ultrasonic vibration applied thereto, and a cleaning mechanism that supplies wafers W with a cleaning solution in the form of spray having a liquid-gas mixture. The constructions of these cleaning mechanisms will be described sequentially. The front surface cleaning units 15 and back surface cleaning units 16 may have one or more of these cleaning mechanisms.

Figure 11:
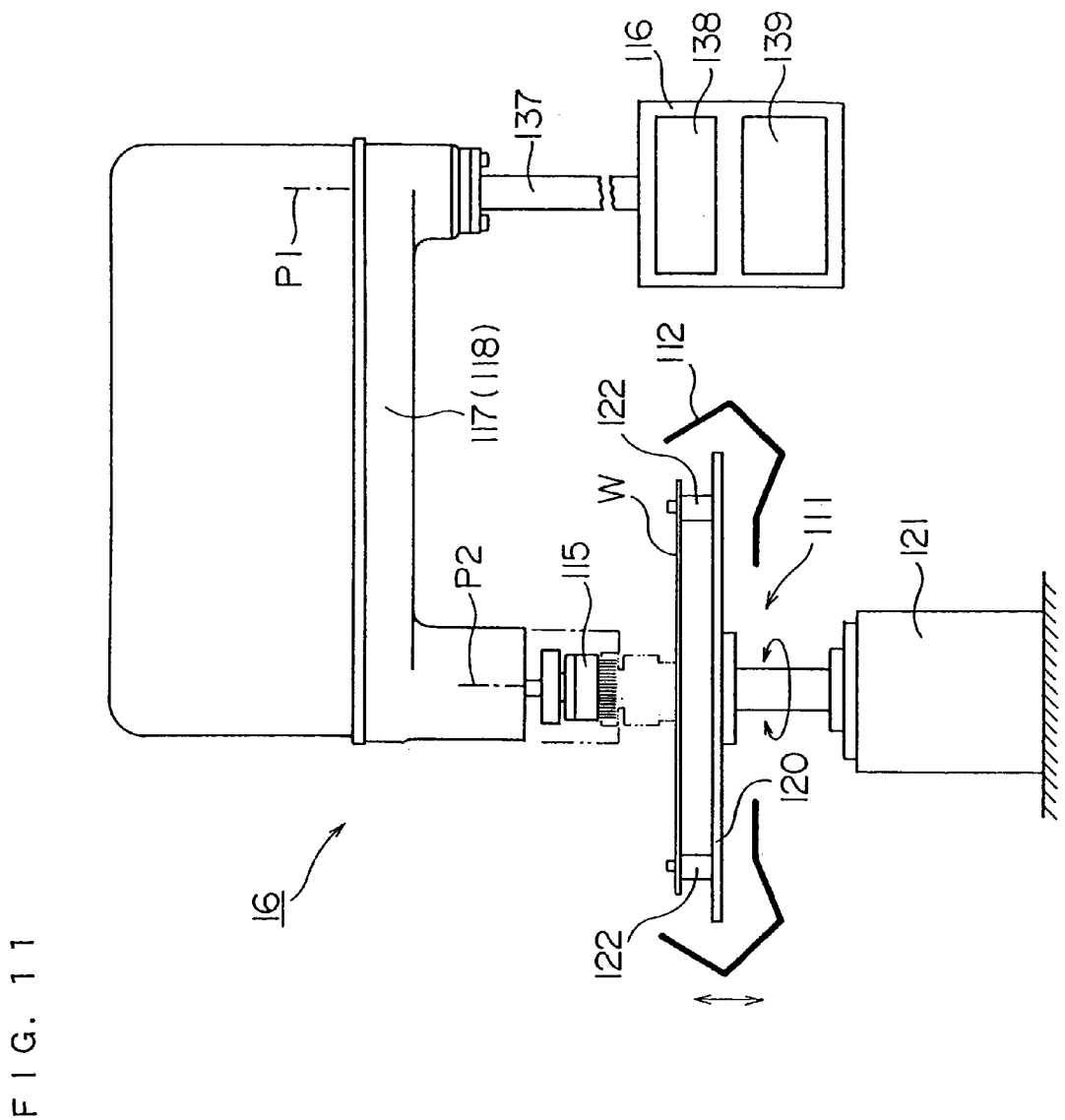
FIG. 11 is a view in vertical section showing an outline of a back surface cleaning unit.

An embodiment will be described first, in which each back surface cleaning unit 16 employs the cleaning mechanism that cleans wafers W with a cleaning brush. FIG. 11 is a view in vertical section schematically showing an outline of such back surface cleaning unit 16.

This back surface cleaning unit 16 includes a spin chuck 111 for rotatably supporting a wafer W, a cup 112 vertically movably disposed around the wafer W supported by the spin chuck 111 for preventing scattering of a cleaning solution, a cleaning solution supply nozzle, not shown, for supplying the cleaning solution to the wafer W supported by the spin chuck 111, a cleaning brush 115 for cleaning the wafer W with the cleaning solution supplied from the cleaning solution supply nozzle, a moving mechanism 116 for moving the cleaning brush 115 along the back surface of the wafer W supported by the spin chuck 111, and a pressure adjusting mechanism 118 mounted in a support arm 117 for adjusting a pressing force of the cleaning brush 115 applied to the wafer W supported by the spin chuck 111.

The spin chuck 111 is driven by a motor 121 to spin about a vertical axis. The spin chuck 111 has a plurality of support pins 122 erected on a base 120. The wafer W is supported by the support pins 122 of the spin chuck 111.

The cleaning brush 115 is supported at the distal end of angle type support arm 117 to be rotatable about a vertical axis P2. This cleaning brush 115 has a working brush portion formed of nylon, mohair, sponge, felt or plastic. The support arm 117 is pivotable about a vertical axis P1 located outwardly of the scatter preventive cup 112.

The proximal end of support arm 117 is connected to an upper end of a support shaft 137 to be rotatable therewith. The pivotal movement about the axis P1 of the support arm 117 is caused by a reversible motor 138 of the moving mechanism 116 through the support shaft 137. With this pivotal movement, the cleaning brush 115 is moved horizontally between a standby position laterally of the scatter preventive cup 112 and a position over the wafer W supported by the spin chuck 111. The cleaning brush 115 is also movable horizontally, in time of cleaning the wafer W, to sweep over a film of cleaning solution formed on the wafer W.

The moving mechanism 116 includes a mechanism 139 for monitoring a position of the cleaning brush 115. This position monitoring mechanism 139 has a rotary encoder, for example, for monitoring an absolute angle θ of the support arm 117 pivoting about the axis P1. The absolute angle θ of the support arm 117 and the position of the cleaning brush 115 over the wafer W are in a corresponding relationship. The position of the cleaning brush 115 cleaning the wafer W may therefore be determined by monitoring the absolute angle θ of the support arm 117.

Figure 12:
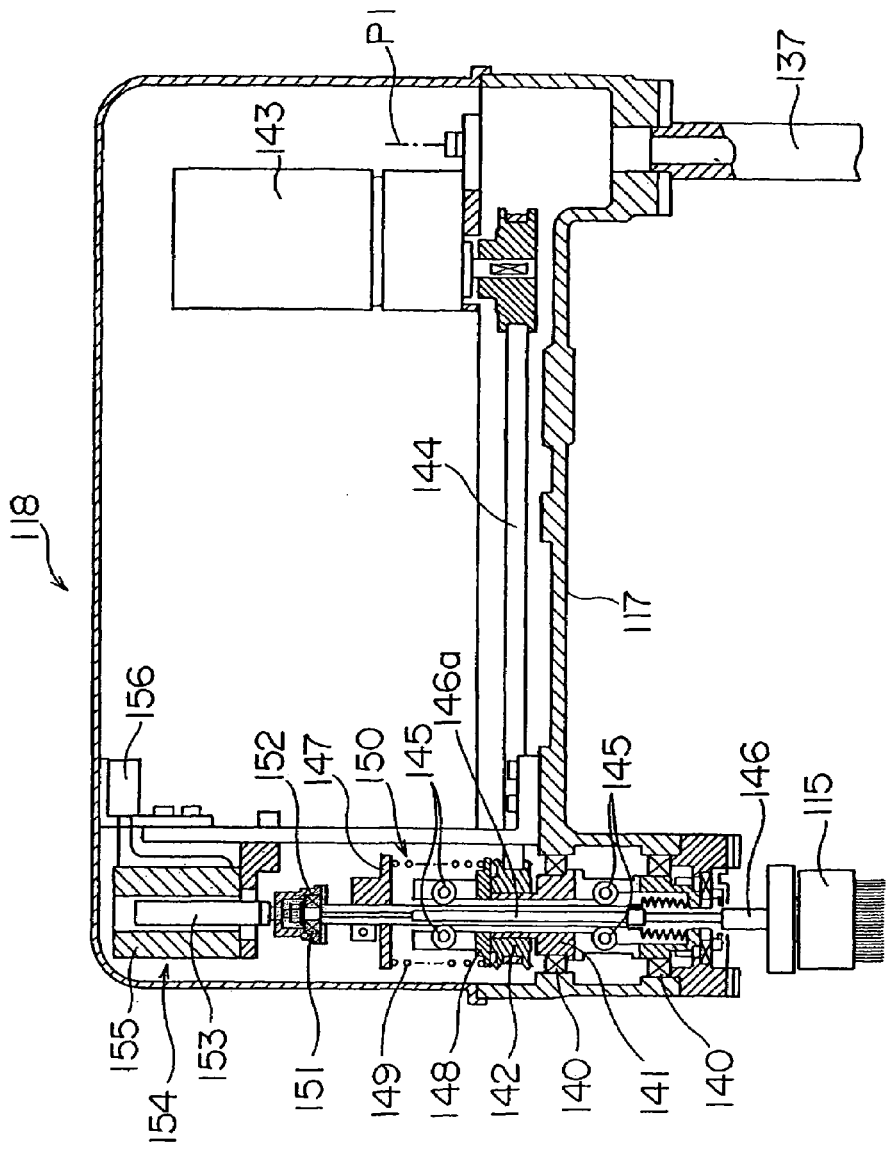
FIG. 12 is a sectional view showing a pressure adjusting mechanism and a brush rotating mechanism arranged in a support arm.

The pressure adjusting mechanism 118 for adjusting a pressing force of the cleaning brush 115 applied to the wafer W supported by the spin chuck 111 will be described next. FIG. 12 is a sectional view showing the pressure adjusting mechanism 118 and a brush rotating mechanism arranged in the support arm 117.

As shown in FIG. 12, the support arm 117 has a rotating element 141 supported therein through a bearing 140 to be rotatable about the axis P2. The rotating element 141 has a pulley 142 fixed thereto and interlocked to a motor 143 through a timing belt 144. Two pairs of guide rollers 145 are arranged in upper and lower positions across the pulley 142 on the rotating element 141. These guide rollers 145 act on splines 146a formed on an intermediate portion of a cleaning brush support 146 carrying the cleaning brush 115 at the lower end thereof. Thus, the brush support 146 is vertically movable while rotating with the rotating element 141.

The brush support 146 has a spring seat 147 mounted to be rotatable therewith, and the rotating element 141 has a spring seat 148 mounted thereon. A compression coil spring 149 extends between these spring seats 147 and 148 to balance the weight of the cleaning brush 115 and brush support 146. Thus, a weight balancing mechanism 150 is formed for maintaining the cleaning brush 115 at a predetermined height relative to the support arm 17.

Further, the brush support 146 has an abutting member 152 mounted at the upper end thereof only to be rotatable relative to the brush support 146 through a bearing 151. The abutting member 152 is connected at the upper end thereof to a control rod 153. The control rod 153 extends through a coil 155 to constitute a linear actuator 154.

Figure 13:
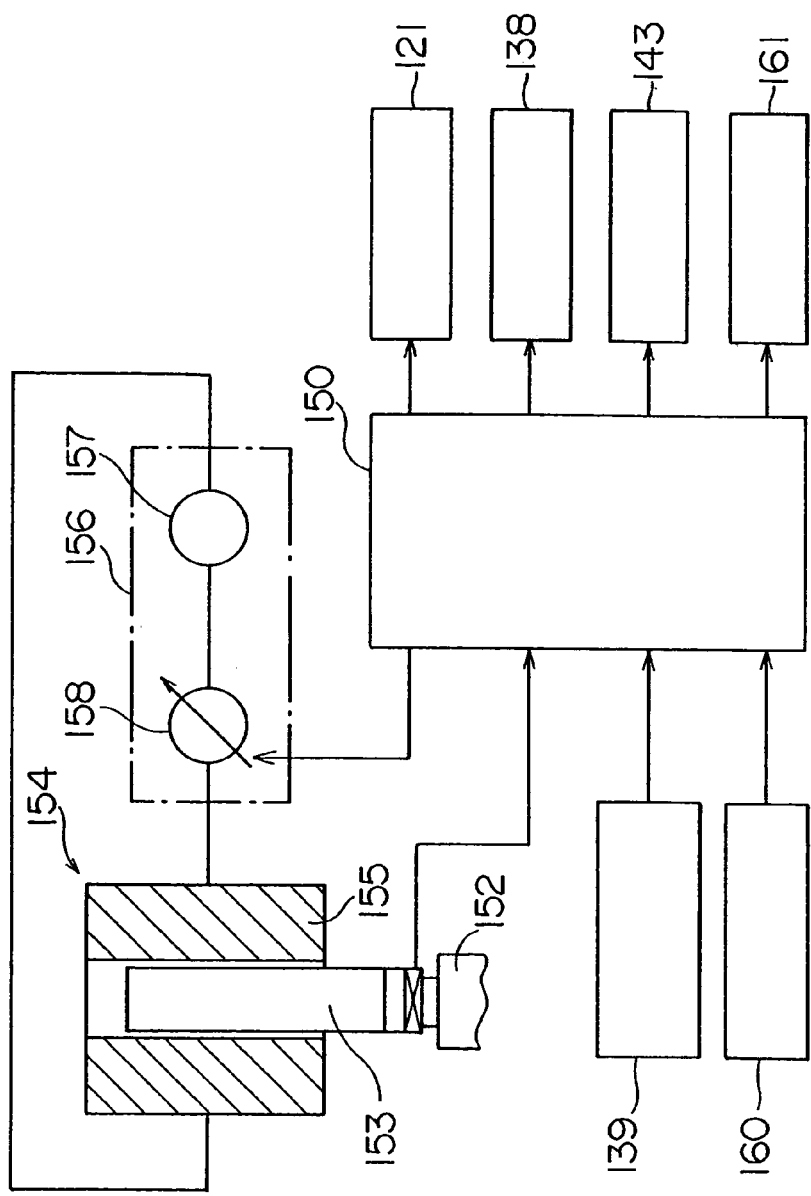
FIG. 13 is a block diagram of a main electrical construction of the back surface cleaning unit including the pressure adjusting mechanism.

FIG. 13 is a block diagram of a main electrical construction of the back surface cleaning unit 16 including the pressure adjusting mechanism 118.

As seen, the linear actuator 154 is connected to a power supply unit 156 including a power source 157 and a variable resistor 158. By adjusting the resistance of variable resistor 158, the current applied to the coil 155 is varied to adjust the electromagnetic force of the linear actuator 154, thereby to move the control rod 153 linearly up and down to an adjusted height. Through the brush support 146, the cleaning brush 115 is moved up and down to an adjusted height. The cleaning brush 115 may apply to the wafer W a pressing load (i.e. pressing force) corresponding to the height of the cleaning brush 115. During a cleaning operation, the cleaning pressure of the cleaning brush 115 applied to the wafer W may be varied as desired, by varying the resistance of variable resistor 158.

The resistance of variable resistor 158 in the power supply unit 156 is adjusted by the controller 150. The controller 150 receives monitoring information from the position monitoring mechanism 139, and controls the motors 121, 138 and 143 and a cleaning solution supply unit 161 that supplies the cleaning solution to the cleaning solution supply nozzle. The controller 150 has also a pressing load setter 160 connected thereto.

For cleaning the wafer W, the pressing load setter 160 is operated to set a pressing force (i.e. pressing load) appropriate to the type of film formed on the wafer W (e.g. aluminum film, oxide film, nitride film, polysilicon film, pattern film or bare silicon) or the property and type of contaminant adhering to the wafer W. This pressing force is set according to the position of the cleaning brush 115 relative to the wafer W supported by the spin chuck 111.

Thus, in time of cleaning the wafer W, the controller 150 controls the power supply unit 156 to adjust the electromagnetic force of the linear actuator 154, and adjust the height of the control rod 153, thereby to move the cleaning brush 115 up and down through the brush support 146 to an adjusted height. The wafer W supported by the spin chuck 111 is cleaned by the cleaning brush 115 applying the pressing load (pressing force) set beforehand according to the position of the cleaning brush 115 relative to the wafer W.

When the wafer W is cleaned by the back surface cleaning unit 16 having the above construction, the spin chuck 111 is spun by the motor 121, and the cleaning solution is supplied to the wafer W from the cleaning solution supply nozzle not shown. The cleaning arm 117 is driven by the motor 138 to pivot about the axis P1 to move the cleaning brush 115 horizontally from the standby position to a position over the spin center of wafer W. Subsequently, the resistance of variable resistor 158 is adjusted to cause the cleaning brush 115 to act on the wafer W with the predetermined pressing force.

In this state, while operating the motor 143 to rotate the cleaning brush 115 about the axis P2, the electric motor 138 is operated to move the cleaning brush 115 at a fixed speed and horizontally over the film of cleaning solution formed on the wafer W, thereby cleaning the wafer W.

In carrying out such a cleaning operation, the controller 150 adjusts the spinning speed of the spin chuck 111, the rotating speed of the cleaning brush 115, and the pressing force of the cleaning brush 115 in order to clean the wafer W with a maximum effect.

Figure 14:
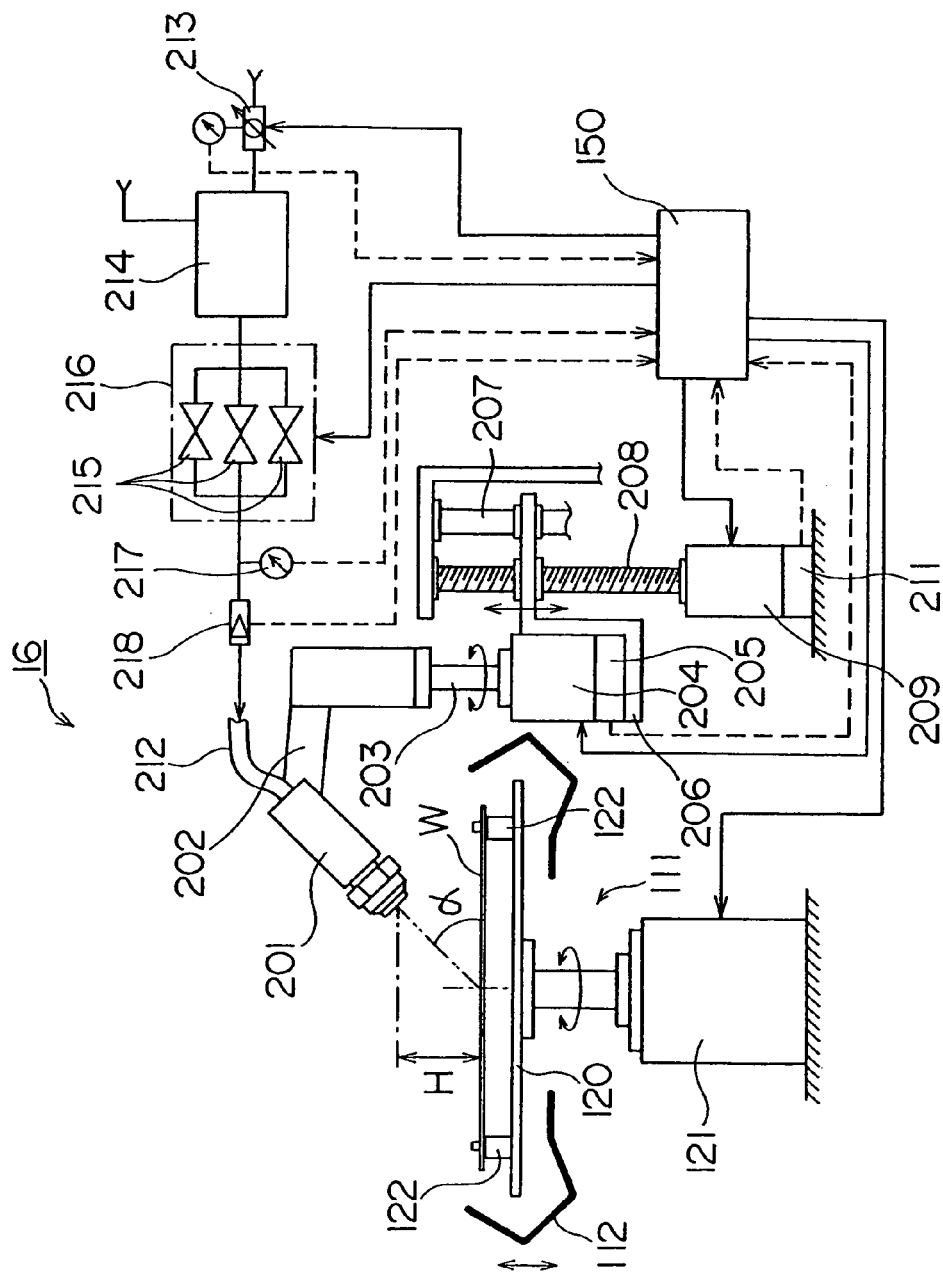
FIG. 14 is a view in vertical section showing an outline of a modified back surface cleaning unit.

Next, an embodiment will be described in which each back surface cleaning unit 16 employs the cleaning mechanism that supplies wafers W with a cleaning solution under high pressure. FIG. 14 is a view in vertical section schematically showing an outline of such back surface cleaning unit 16.

This back surface cleaning unit 16 includes a spin chuck 111 for rotatably supporting a wafer W, a cup 112 vertically movably disposed around the wafer W supported by the spin chuck 111 for preventing scattering of the cleaning solution, a cleaning solution supply nozzle 201 for supplying the cleaning solution under high pressure to the wafer W supported by the spin chuck 111.

The spin chuck 111 is driven by a motor 121 to rotate about a vertical axis. The spin chuck 111 has a plurality of support pins 122 erected on a base 120. The wafer W is supported by the support pins 122 of the spin chuck 111.

The cleaning solution supply nozzle 201 is supported at the distal end of a support arm 202. The proximal end of support arm 202 is connected to an upper end of a shaft 203 to be rotatable therewith. The support arm 202 is pivotable about the shaft 203 by a reversible motor 204. With this pivotal movement, the cleaning solution supply nozzle 201 is moved horizontally between a standby position laterally of the scatter preventive cup 112 and a position over the wafer W supported by the spin chuck 111.

The motor 204 has a rotary encoder 205 attached thereto. This rotary encoder 205 monitors, for example, an absolute angle θ of the support arm 202 pivoting about the shaft 203. The absolute angle θ of the support arm 202 and the position of the cleaning solution supply nozzle 201 over the wafer W are in a corresponding relationship. The position of the supply nozzle 201 cleaning the wafer W may therefore be determined by monitoring the absolute angle θ of the support arm 202.

The motor 204 and rotary encoder 205 are supported on a lift base 206. The lift base 206 is slidably fitted on a vertical guide rod 207 and meshed with a ball screw 208 extending parallel to the guide rod 207. The ball screw 208 is operatively connected to a rotary shaft of a lift motor 209. An amount of rotation of the lift motor 209 is detected by a rotary encoder 211. When the lift motor 209 is operated with the cleaning solution supply nozzle 201 located in a cleaning position over the wafer W, the supply nozzle 201 is vertically moved to adjust a height of the discharge opening of supply nozzle 201 (discharge height H) above the surface of wafer W.

The cleaning solution is supplied to the nozzle 201 through piping 212. The piping 212 includes a high-pressure unit 214 for adjusting a pressure of the cleaning solution from a cleaning solution source not shown, according to a pressure received from an electropneumatic change valve 213, a flow control unit 216 having a plurality of electromagnetic valves 215 disposed on separate flow paths for adjusting a flow rate of the cleaning solution, a pressure sensor 217 for detecting a pressure of the cleaning solution outputted from the flow control unit 216, and a flow rate sensor 218 for detecting a flow rate of the cleaning solution.

The electropneumatic change valve 213 receives an electric signal from a controller 150 to adjust an air pressure to a pressure corresponding to the electric signal. The adjusted pressure is detected by a pressure sensor provided for the electropneumatic change valve 213, which is fed back to the controller 150. Detection signals of pressure sensor 217 and flow rate sensor 218 also are fed back to the controller 150 for controlling the high-pressure unit 214 and flow control unit 216.

When the wafer W is cleaned by the back surface cleaning unit 16 having the above construction, the spin chuck 111 is spun by the motor 121, the cleaning solution is supplied to the wafer W from the cleaning solution supply nozzle 201. The motor 204 is operated to cause the nozzle 201 to pivot horizontally about the shaft 203 and supply the cleaning solution under high pressure to the wafer W, thereby to clean the wafer W.

In carrying out such a cleaning operation, the controller 150 adjusts the spinning speed of the spin chuck 111, and the pressure, discharge rate and discharge height H of the cleaning solution supplied from the cleaning solution supply nozzle 201, in order to clean the wafer W with a maximum effect. Further, an angle to the surface of wafer W of the cleaning solution supply nozzle 201 (discharge angle α) may be varied.

Figure 15:
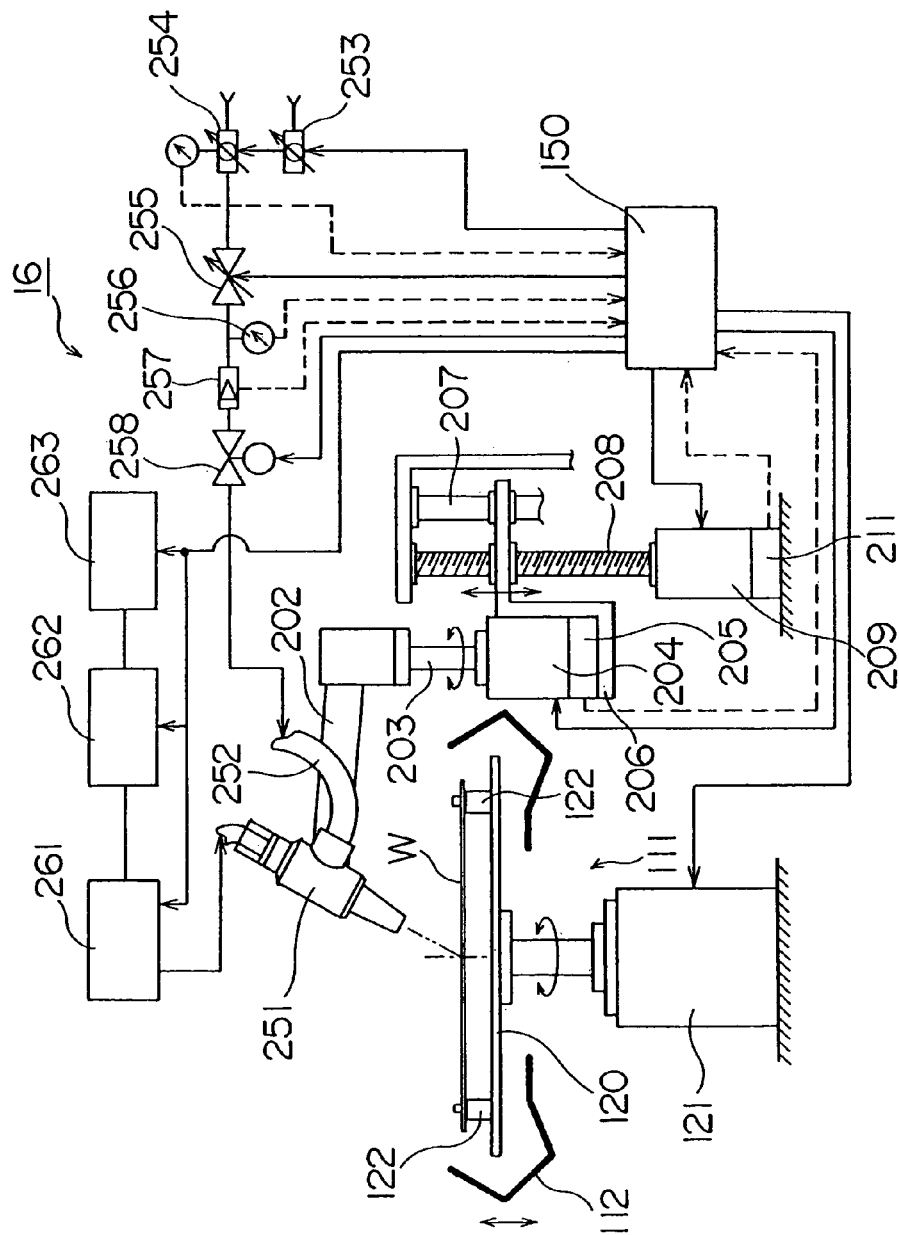
FIG. 15 is another view in vertical section showing an outline of another modified back surface cleaning unit.

Next, an embodiment will be described in which each back surface cleaning unit 16 employs the cleaning mechanism that supplies wafers W with a cleaning solution with ultrasonic vibration applied thereto. FIG. 15 is a view in vertical section schematically showing an outline of such back surface cleaning unit 16.

This back surface cleaning unit 16 includes a spin chuck 111 for rotatably supporting a wafer W, a cup 112 vertically movably disposed around the wafer W supported by the spin chuck 111 for preventing scattering of the cleaning solution, a cleaning solution supply nozzle 251 for supplying the cleaning solution under high pressure to the wafer W supported by the spin chuck 111.

The spin chuck 111 is driven by a motor 121 to spin about a vertical axis. The spin chuck 111 has a plurality of support pins 122 erected on a base 120. The wafer W is supported by the support pins 122 of the spin chuck 111.

The cleaning solution supply nozzle 251 is supported at the distal end of a support arm 202. The proximal end of support arm 202 is connected to an upper end of a shaft 203 to be rotatable therewith. The support arm 202 is pivotable about the shaft 203 by a reversible motor 204. With this pivotal movement, the cleaning solution supply nozzle 251 is moved horizontally between a standby position laterally of the scatter preventive cup 112 and a position over the wafer W supported by the spin chuck 111.

The motor 204 has a rotary encoder 205 attached thereto. This rotary encoder 205 monitors, for example, an absolute angle θ of the support arm 202 pivoting about the shaft 203. The absolute angle θ of the support arm 202 and the position of the cleaning solution supply nozzle 251 over the wafer W are in a corresponding relationship. The position of the supply nozzle 251 cleaning the wafer W may therefore be determined by monitoring the absolute angle θ of the support arm 202.

The motor 204 and rotary encoder 205 are supported on a lift base 206. The lift base 206 is slidably fitted on a vertical guide rod 207 and meshed with a ball screw 208 extending parallel to the guide rod 207. The ball screw 208 is operatively connected to a rotary shaft of a lift motor 209. An amount of rotation of the lift motor 209 is detected by a rotary encoder 211. When the lift motor 209 is operated with the cleaning solution supply nozzle 251 located in a cleaning position over the wafer W, the supply nozzle 251 is vertically moved to adjust a height of the discharge opening of supply nozzle 251 (discharge height H) above the surface of wafer W.

The cleaning solution is supplied to the nozzle 251 through piping 252. The piping 252 includes a pressure control valve 254 for adjusting a pressure of the cleaning solution from a cleaning solution source not shown, according to a pressure received from an electropneumatic change valve 253, a flow control valve 255 for adjusting a flow rate of the cleaning solution as instructed by a controller 150, a pressure sensor 256 for detecting a pressure of the cleaning solution, a flow rate sensor 257 for detecting a flow rate of the cleaning solution, and a switch valve 258 operable by the controller 150 to supply or stop the cleaning solution from the supply nozzle 251.

The electropneumatic change valve 253 receives an electric signal from the controller 150 to adjust an air pressure to a pressure corresponding to the electric signal. The adjusted pressure is detected by a pressure sensor provided for the pressure control valve 254, which is fed back to the controller 150. Detection signals of pressure sensor 256 and flow rate sensor 257 also are fed back to the controller 150 for controlling the electropneumatic change valve 253 and flow control valve 255.

The cleaning solution supply nozzle 251 has a plurality of vibrators arranged therein and having different resonance frequencies for applying ultrasonic vibration to the cleaning solution. These vibrators are connected to a vibrator selector 261. Each vibrator receives a high frequency voltage of a predetermined frequency through an oscillator 263 and an amplifier 262 controlled by the controller 150. Since the vibrators have different resonance frequencies, the controller 29 operates the vibrator selector 261 according to a frequency, whereby the high frequency voltage is applied only to the vibrator having the same resonance frequency as that frequency.

The oscillator 263 is constructed to oscillate in a given frequency corresponding to a signal inputted from the controller 150. The amplifier 262 is constructed to amplify a high frequency signal from the oscillator 263 to an amplitude corresponding to a signal inputted from the controller 150. That is, the ultrasonic frequency and output are adjustable on instructions from the controller 150.

When the wafer W is cleaned by the back surface cleaning unit 16 having the above construction, the spin chuck 111 is spun by the motor 121, the cleaning solution is supplied to the wafer W from the cleaning solution supply nozzle 251. The motor 204 is operated to cause the nozzle 251 to pivot horizontally about the shaft 203 and supply the cleaning solution with ultrasonic vibration applied thereto to the wafer W, thereby to clean the wafer W.

In carrying out such a cleaning operation, the controller 150 adjusts the spinning speed of the spin chuck 111, the pressure, discharge rate and discharge height H of the cleaning solution supplied from the cleaning solution supply nozzle 251, the discharge height H, and the ultrasonic frequency and output applied to the cleaning solution, in order to clean the wafer W with a maximum effect.

Figure 16:
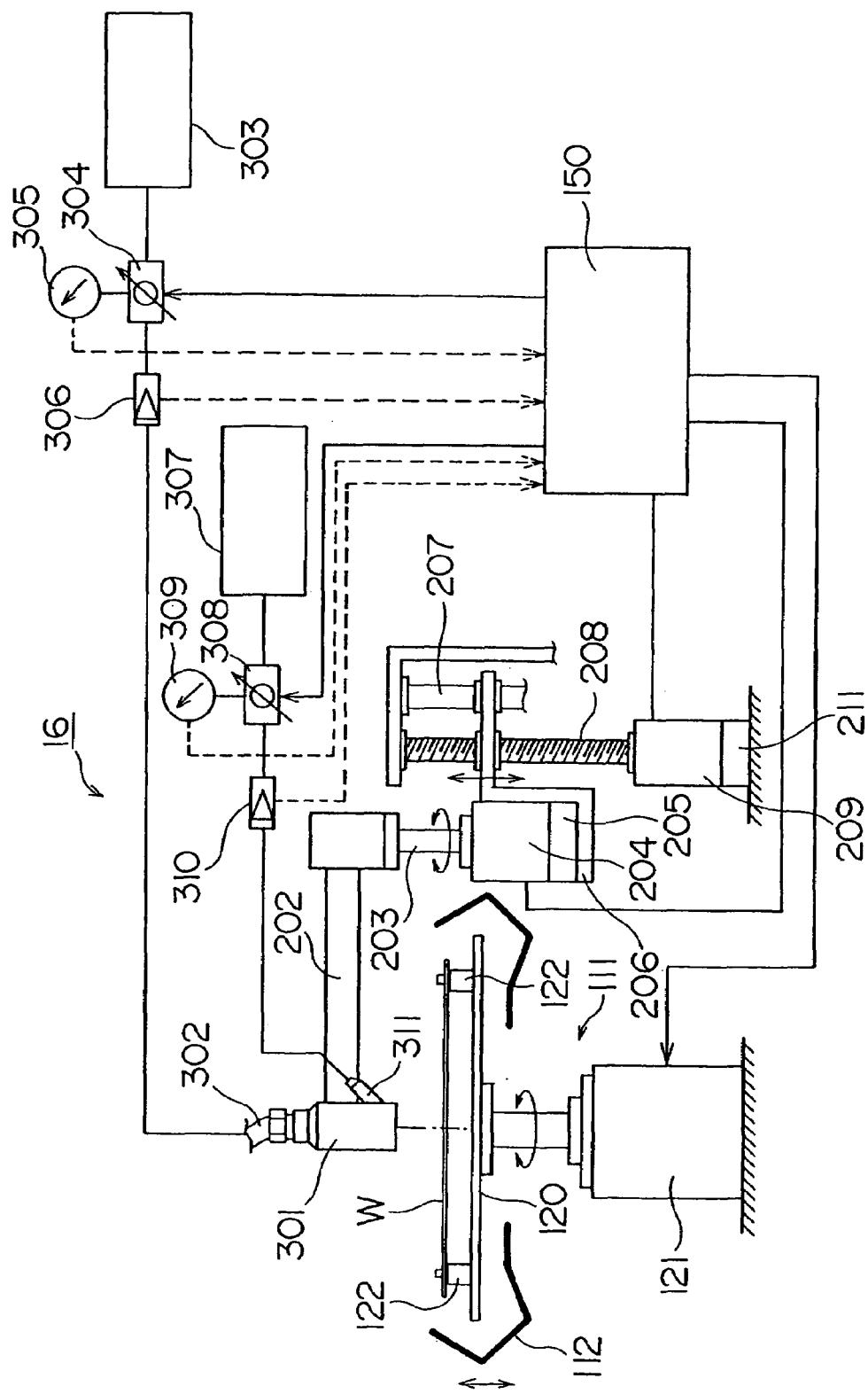
FIG. 16 is yet another view in vertical section showing an outline of a further modified back surface cleaning unit.

Next, an embodiment will be described in which each back surface cleaning unit 16 employs the cleaning mechanism that supplies wafers W with a cleaning solution in the form of spray having a liquid-gas mixture. FIG. 16 is a view in vertical section schematically showing an outline of such back surface cleaning unit 16.

This back surface cleaning unit 16 includes a spin chuck 111 for rotatably supporting a wafer W, a cup 112 vertically movably disposed around the wafer W supported by the spin chuck 111 for preventing scattering of the cleaning solution, a cleaning solution supply nozzle 301 for supplying the cleaning solution in the form of spray having a liquid-gas mixture to the wafer W supported by the spin chuck 111.

The spin chuck 111 is driven by a motor 121 to spin about a vertical axis. The spin chuck 111 has a plurality of support pins 122 erected on a base 120. The wafer W is supported by the support pins 122 of the spin chuck 111.

The cleaning solution supply nozzle 301 is supported at the distal end of a support arm 202. The proximal end of support arm 202 is connected to an upper end of a shaft 203 to be rotatable therewith. The support arm 202 is pivotable about the shaft 203 by a reversible motor 204. With this pivotal movement, the cleaning solution supply nozzle 301 is moved horizontally between a standby position laterally of the scatter preventive cup 112 and a position over the wafer W supported by the spin chuck 111.

The motor 204 has a rotary encoder 205 attached thereto. This rotary encoder 205 monitors, for example, an absolute angle θ of the support arm 202 pivoting about the shaft 203. The absolute angle θ of the support arm 202 and the position of the cleaning solution supply nozzle 301 over the wafer W are in a corresponding relationship. The position of the supply nozzle 301 cleaning the wafer W may therefore be determined by monitoring the absolute angle θ of the support arm 202.

The motor 204 and rotary encoder 205 are supported on a lift base 206. The lift base 206 is slidably fitted on a vertical guide rod 207 and meshed with a ball screw 208 extending parallel to the guide rod 207. The ball screw 208 is operatively connected to a rotary shaft of a lift motor 209. An amount of rotation of the lift motor 209 is detected by a rotary encoder 211. When the lift motor 209 is operated with the cleaning solution supply nozzle 301 located in a cleaning position over the wafer W, the supply nozzle 301 is vertically moved to adjust a height of the discharge opening of supply nozzle 301 (discharge height H) above the surface of wafer W.

The cleaning solution supply nozzle 301 is a binary fluid nozzle connected to piping 302 for introducing compressed air acting as a gas, and piping 311 for supplying deionized water as a liquid.

The piping 302 is connected to a compressed air source 303. The piping 302 includes an electropneumatic regulator 304 for adjusting a pressure of air flowing therethrough to a pressure corresponding to a control signal inputted from a controller 150, a pressure sensor 305 for detecting a pressure of the air, and a flow rate sensor 306 for detecting a flow rate of the air.

The piping 311 is connected to a deionized water source 307. This piping 311 includes an electropneumatic regulator 308 for adjusting a pressure of deionized water flowing therethrough to a pressure corresponding to a control signal inputted from the controller 150, a pressure sensor 309 for detecting a pressure of the deionized water, and a flow rate sensor 310 for detecting a flow rate of the deionized water. It is to be noted that ultrapure water or a chemical solution may be used instead of deionized water.

Figure 17:
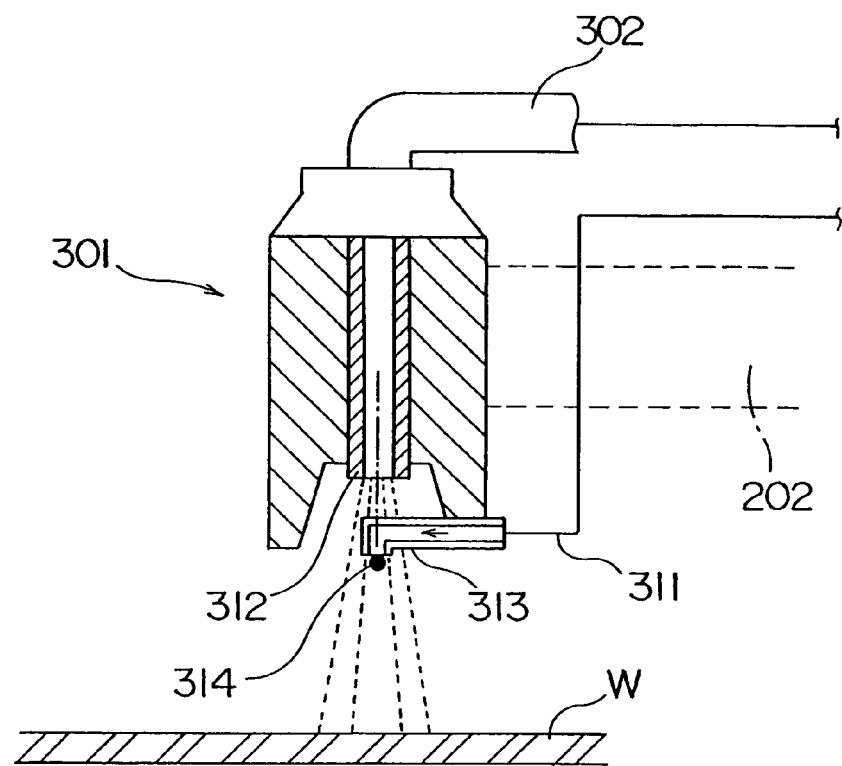
FIG. 17 is a view schematically showing an internal structure of a cleaning solution supply nozzle.

FIG. 17 is a view schematically showing an internal structure of the cleaning solution supply nozzle 301.

The supply nozzle 301 includes a gas delivery member 312 connected to the piping 302 for introducing the compressed air, and a liquid delivery member 313 connected to the piping 311 for supplying the deionized water. The liquid delivery member 313 has a tip end thereof disposed under the gas delivery member 312 and within an air current discharged from the gas delivery member 312. Consequently, the deionized water discharged from the liquid delivery member 313 is quickly reduced to droplets by surrounding jet streams of air in a position 314 under the liquid delivery member 313. The droplets of deionized water and the air constitute the cleaning solution in the form of spray to be supplied to the wafer W to clean the latter.

In carrying out such a cleaning operation, the controller 150 adjusts the spinning speed of the spin chuck 111, the flow rate of the compressed air acting as the gas supplied to the supply nozzle 301, the flow rate of the deionized water acting as the liquid supplied to the supply nozzle 301, and the discharge height H, in order to clean the wafer W with a maximum effect.

As described above, each back surface cleaning unit 16 may use the cleaning mechanism for cleaning wafers W with a cleaning brush, the cleaning mechanism that supplies wafers W with a cleaning solution under high pressure, the cleaning mechanism that supplies wafers W with a cleaning solution with ultrasonic vibration applied thereto, or the cleaning mechanism that supplies wafers W with a cleaning solution in the form of spray having a liquid-gas mixture. Whichever cleaning mechanism is used, a cleaning operation may be controlled in a way to clean the wafers W with a maximum effect. This applies also to the front surface cleaning units 15 different only in the configuration of the spin chuck.

Figure 18:
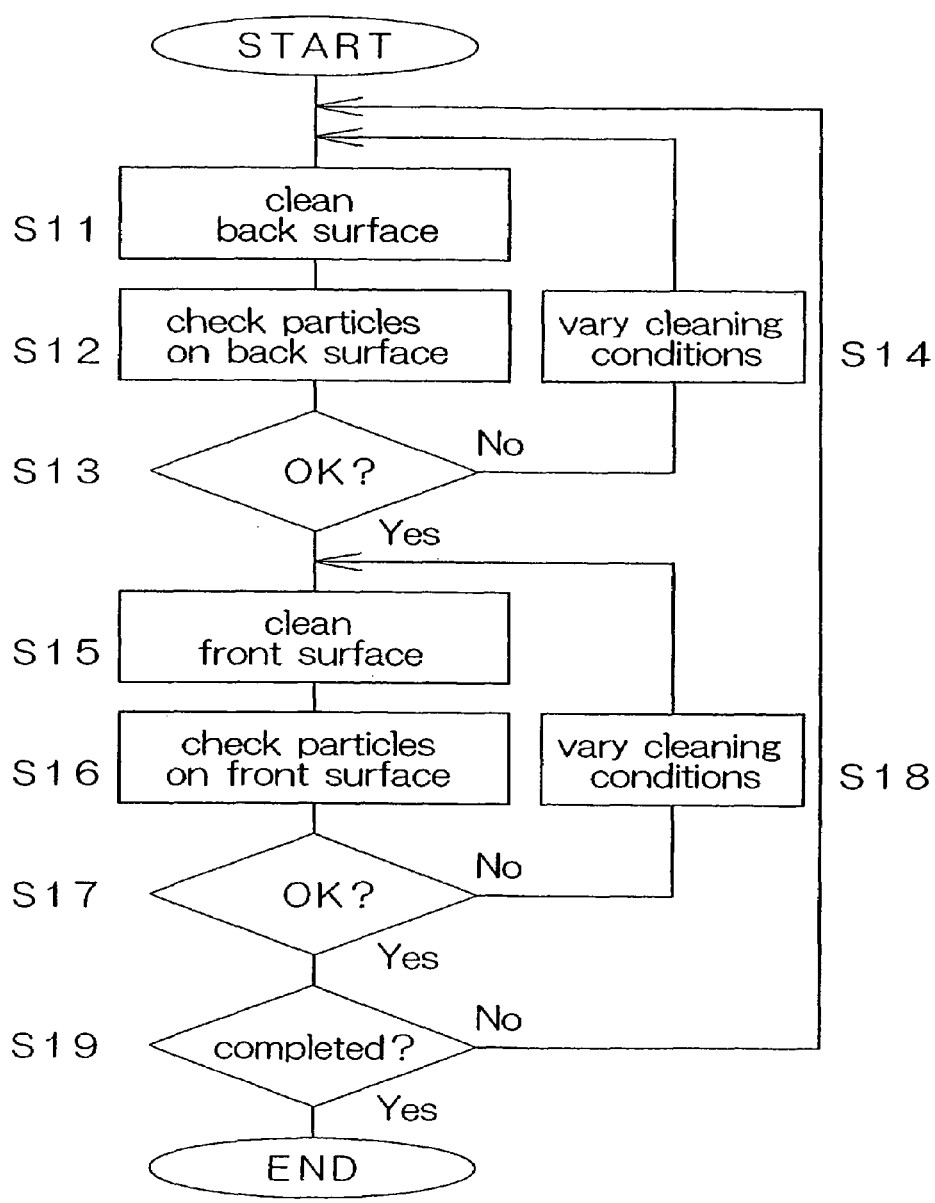
FIG. 18 is a flow chart of a substrate cleaning operation.

Next, an operation of the above substrate cleaning apparatus for cleaning a wafer W will be described next. FIG. 18 is a flow chart of the operation of the substrate cleaning apparatus for cleaning a wafer W.

With this substrate processing apparatus, a wafer W taken out of a cassette 10 is cleaned, and then whether the wafer W is cleaned sufficiently is determined by detecting a distribution of particles on the wafer W. When the wafer W is found not sufficiently clean, cleaning conditions of the cleaning unit are varied according to the distribution of particles. The wafer W is cleaned with varied cleaning conditions until the wafer W becomes sufficiently clean. Such an operation is carried out for the back surface and front surface of the wafer W, thereby effectively cleaning both surfaces of the wafer W.

When cleaning the wafer W with this substrate cleaning apparatus, the back surface of wafer W is cleaned first (step S11). The transport unit 13 takes the wafer W out of a cassette 10 placed on the indexer 11, and passes the wafer W on to the transport unit 12. When the wafer W has the front surface thereof facing up in the cassette 10, this wafer W is transported to the reversing unit 18 first, where the wafer W is reversed from the position with the front surface facing up to a position with the back surface facing up. Then, the wafer W is transported to one of the back surface cleaning units 16 to have the back surface cleaned. On the other hand, when the wafer W has the back surface thereof facing up in the cassette 10, the wafer W is transported to one of the back surface cleaning units 16 first to have the back surface cleaned.

Next, a distribution of particles on the back surface of wafer W is detected (step S12). Specifically, the transport unit 12 transports the wafer W with the back surface cleaned to one of the particle inspecting units 17 for inspecting a distribution of particles adhering to the cleaned back surface of wafer W.

Whether the back surface of wafer W is sufficiently clean is determined from the distribution of particles detected (step S13).

When the back surface of wafer W is found not sufficiently clean, the transport unit 12 transports the wafer W to the back surface cleaning unit 16 again. On the other hand, data of the distribution of particles on the cleaned back surface of wafer W measured by the particle inspecting unit 17 is transmitted to the controller 150 of the back surface cleaning unit 16 having cleaned the wafer W. Based on this data, the controller 150 of the back surface cleaning unit 16 varies the cleaning conditions of the back surface cleaning unit 16 for cleaning the wafer W (step S14). Then, the back surface of wafer W is cleaned with the new cleaning conditions.

More particularly, for the back surface cleaning unit 16 shown in FIGS. 11 through 13, the controller 150 adjusts the spinning speed of spin chuck 111, the rotating speed of cleaning brush 115, and the pressing force of cleaning brush 115. For the back surface cleaning unit 16 shown in FIG. 14, the controller 150 adjusts the spinning speed of spin chuck 111, and the pressure, discharge rate and discharge height H of the cleaning solution supplied from the cleaning solution supply nozzle 201. For the back surface cleaning unit 16 shown in FIG. 15, the controller 150 adjusts the spinning speed of spin chuck 111, the pressure, discharge rate and discharge height H of the cleaning solution supplied from the cleaning solution supply nozzle 251, and the ultrasonic frequency and output applied to the cleaning solution. For the back surface cleaning unit 16 shown in FIGS. 16 and 17, the controller 150 adjusts the spinning speed of spin chuck 111, the flow rate of compressed air acting as a gas supplied to the cleaning solution supply nozzle 301, the flow rate of deionized water acting as a liquid supplied to the cleaning solution supply nozzle 301, and the discharge height H.

Steps S11 through S14 are repeated until the back surface of wafer W is determined to be sufficiently clean from a distribution of particles detected in step S12. That is, the wafer W is repeatedly cleaned in the back surface cleaning unit 16 until it is cleaned sufficiently.

After the back surface of wafer W is sufficiently cleaned as a result of varying the cleaning conditions of the back surface cleaning unit 16, the front surface of wafer W is cleaned (step S15). That is, the wafer W with the back surface thereof determined to be sufficiently clean as a result of inspection by the particle inspecting unit 17 is transported by the transport unit 12 from the particle inspecting unit 17 to the reversing unit 18 where the wafer W is reversed from the position with the back surface facing up to a position with the front surface facing up. The reversed wafer W is transported by the transport unit 12 from the reversing unit 18 to one of the front surface cleaning units 15 to have the front surface cleaned.

Next, a distribution of particles on the front surface of wafer W is detected (step S16). Specifically, the transport unit 12 transports the wafer W with the front surface cleaned to one of the particle inspecting units 17 for inspecting a distribution of particles adhering to the cleaned front surface of wafer W.

Whether the front surface of wafer W is sufficiently clean is determined from the distribution of particles detected (step S17).

When the front surface of wafer W is found not sufficiently clean, the transport unit 12 transports the wafer W to the front surface cleaning unit 15 again. On the other hand, data of the distribution of particles on the cleaned front surface of wafer W measured by the particle inspecting unit 17 is transmitted to the controller 150 of the front surface cleaning unit 15 having cleaned the wafer W. Based on this data, the controller 150 of the front surface cleaning unit 15 varies the cleaning conditions of the front surface cleaning unit 15 for cleaning the wafer W (step S18). Then, the front surface of wafer W is cleaned with the new cleaning conditions.

Steps S15 through S18 are repeated until the front surface of wafer W is determined to be sufficiently clean from a distribution of particles detected in step S16. That is, the wafer W is repeatedly cleaned in the front surface cleaning unit 15 until it is cleaned sufficiently.

After the front surface of wafer W is sufficiently cleaned as a result of varying the cleaning conditions of the front surface cleaning unit 15, the wafer W is transported by the transport units 12 and 13 to be stored in a clean cassette 10 placed on the indexer 10. The above operation is repeated until all necessary wafers W are cleaned (step S19).

The first back surface cleaning step (step S11) and the first front surface cleaning step (step S15) executed on the wafer W in the above embodiment correspond to the first cleaning step according to the invention. The back surface particle inspecting step (step S12) and the front surface particle inspecting step (step S16) correspond to the particle inspecting step according to the invention. Each cleaning condition varying step (step S14 and step S17) corresponds to the cleaning condition varying step according to the invention. Each of the second and subsequent back surface cleaning steps (step S11) and front surface cleaning steps (step S15) corresponds to the second cleaning step according to the invention.

Figure 19:
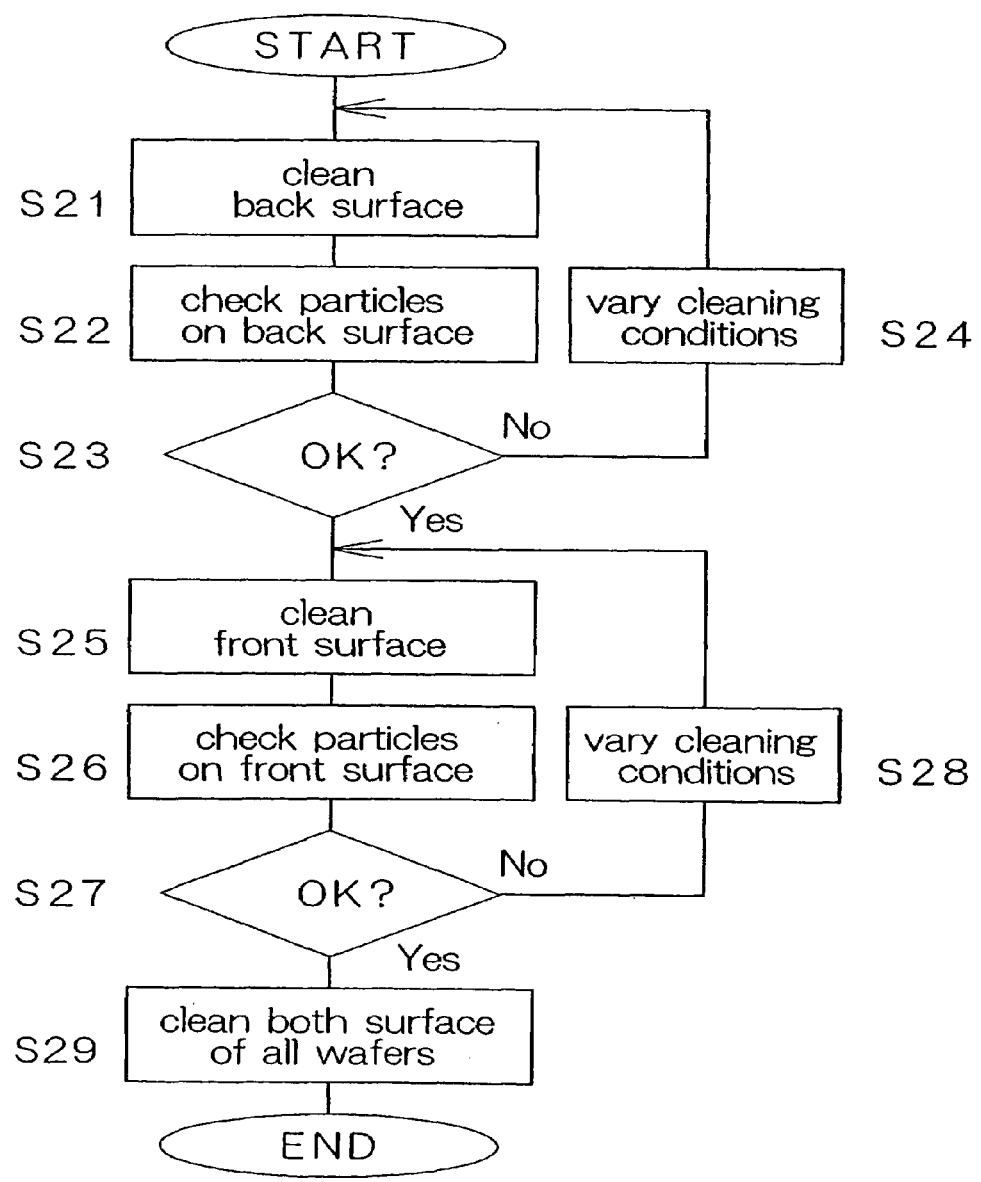
FIG. 19 is a flow chart of a substrate cleaning operation in a different embodiment.

Next, an operation of the above substrate cleaning apparatus for cleaning a wafer W in a different embodiment will be described next. FIG. 19 is a flow chart of the operation of the substrate cleaning apparatus for cleaning a wafer W in the different embodiment.

When cleaning a wafer W, the back surface of wafer W is cleaned first (step S21). The transport unit 13 takes one of the wafers W out of a cassette 10 placed on the indexer 11, and passes this wafer W on to the transport unit 12. When the wafers W have the front surfaces thereof facing up in the cassette 10, this wafer W is transported to the reversing unit 18 first, where the wafer W is reversed from the position with the front surface facing up to a position with the back surface facing up. Then, the wafer W is transported to one of the back surface cleaning units 16 to have the back surface cleaned. On the other hand, when the wafers W have the back surfaces thereof facing up in the cassette 10, the wafer W is transported to one of the back surface cleaning units 16 first to have the back surface cleaned.

Next, a distribution of particles on the back surface of wafer W is detected (step S22). Specifically, the transport unit 12 transports the wafer W with the back surface cleaned to one of the particle inspecting units 17 for inspecting a distribution of particles adhering to the cleaned back surface of wafer W.

Whether the back surface of wafer W is sufficiently clean is determined from the distribution of particles detected (step S23).

When the back surface of wafer W is found not sufficiently clean, data of the distribution of particles on the cleaned back surface of wafer W measured by the particle inspecting unit 17 is transmitted to the controller 150 of the back surface cleaning unit 16 having cleaned the wafer W. Based on this data, the controller 150 of the back surface cleaning unit 16 varies the cleaning conditions of the back surface cleaning unit 16 for cleaning the wafer W (step S24).

More particularly, for the back surface cleaning unit 16 shown in FIGS. 11 through 13, the controller 150 adjusts the spinning speed of spin chuck 111, the rotating speed of cleaning brush 115, and the pressing force of cleaning brush 115. For the back surface cleaning unit 16 shown in FIG. 14, the controller 150 adjusts the spinning speed of spin chuck 111, and the pressure, discharge rate and discharge height H of the cleaning solution supplied from the cleaning solution supply nozzle 201. For the back surface cleaning unit 16 shown in FIG. 15, the controller 150 adjusts the spinning speed of spin chuck 111, the pressure, discharge rate and discharge height H of the cleaning solution supplied from the cleaning solution supply nozzle 251, and the ultrasonic frequency and output applied to the cleaning solution. For the back surface cleaning unit 16 shown in FIGS. 16 and 17, the controller 150 adjusts the spinning speed of spin chuck 111, the flow rate of compressed air acting as a gas supplied to the cleaning solution supply nozzle 301, the flow rate of deionized water acting as a liquid supplied to the cleaning solution supply nozzle 301, and the discharge height H.

Steps S21 through S24 are repeated until the back surface of wafer W is determined to be sufficiently clean from a distribution of particles detected in step S22. That is, the wafer W is repeatedly cleaned in the back surface cleaning unit 16 until it is cleaned sufficiently. Each cycle of steps S21 through S24 is repeated for a different wafer W. However, steps S21 through S24 may be repeated for the same wafer W.

After the back surface of wafer W is sufficiently cleaned as a result of varying the cleaning conditions of the back surface cleaning unit 16, the front surface of wafer W is cleaned (step S25). That is, the wafer W with the back surface thereof determined to be sufficiently clean as a result of inspection by the particle inspecting unit 17 is transported by the transport unit 12 from the particle inspecting unit 17 to the reversing unit 18 where the wafer W is reversed from the position with the back surface facing up to a position with the front surface facing up. The reversed wafer W is transported by the transport unit 12 from the reversing unit 18 to one of the front surface cleaning units 15 to have the front surface cleaned.

Next, a distribution of particles on the front surface of wafer W is detected (step S26). Specifically, the transport unit 12 transports the wafer W with the front surface cleaned to one of the particle inspecting units 17 for inspecting a distribution of particles adhering to the cleaned front surface of wafer W.

Whether the front surface of wafer W is sufficiently clean is determined from the distribution of particles detected (step S27).

When the front surface of wafer W is found not sufficiently clean, data of the distribution of particles on the cleaned front surface of wafer W measured by the particle inspecting unit 17 is transmitted to the controller 150 of the front surface cleaning unit 15 having cleaned the wafer W. Based on this data, the controller 150 of the front surface cleaning unit 15 varies the cleaning conditions of the front surface cleaning unit 15 for cleaning the wafer W (step S28).

Steps S25 through S28 are repeated until the front surface of wafer W is determined to be sufficiently clean from a distribution of particles detected in step S26. That is, the wafer W is repeated cleaned in the front surface cleaning unit 15 until it is cleaned sufficiently. Each cycle of steps S25 through S28 is repeated for a different wafer W. However, steps S25 through S28 may be repeated for the same wafer W.

After the front surface of wafer W is sufficiently cleaned as a result of varying the cleaning conditions of the front surface cleaning unit 15, all wafers W stored in the cassette 10 and remaining to be cleaned are processed in a repeated operation. Each such wafer W has the back surface cleaned in one of the back surface cleaning units 16, and then the front surface cleaned in one of the front surface cleaning units 15 (step S29).

Thus, the transport unit 13 takes a wafer W out of the cassette 10 placed on the indexer 11, and passes this wafer W on to the transport unit 12. When the wafers W have the front surfaces thereof facing up in the cassette 10, this wafer W is transported to the reversing unit 18 first, where the wafer W is reversed from the position with the front surface facing up to a position with the back surface facing up. Then, the wafer W is transported to one of the back surface cleaning units 16 to have the back surface cleaned. On the other hand, when the wafers W have the back surfaces thereof facing up in the cassette 10, the wafer W is transported to one of the back surface cleaning units 16 first to have the back surface cleaned.

The wafer W with the back surface cleaned is transported by the transport unit 12 from the back surface cleaning units 16 to the reversing unit 18 where the wafer W is reversed from the position with the back surface facing up to a position with the front surface facing up. The reversed wafer W is transported by the transport unit 12 from the reversing unit 18 to one of the front surface cleaning units 15 to have the front surface cleaned. After the front surface is cleaned, the wafer W is transported by the transport units 12 and 13 to be stored in a clean cassette 10 placed on the indexer 10.

In the foregoing embodiments, the invention is applied to cleaning apparatus for cleaning both surfaces of each wafer W. The invention is applicable also to apparatus for cleaning only the front surface of each wafer W.

The present invention may be embodied in other specific forms without departing from the spirit or essential attributes thereof and, accordingly, reference should be made to the appended claims, rather than to the foregoing specification, as indicating the scope of the invention.

This application claims priority benefit under 35 U.S.C. Section 119 of Japanese Patent Applications No. 2001-240677 and No. 2001-240678 filed in the Japanese Patent Office on Aug. 8, 2001, the entire disclosure of which is incorporated herein by reference.

What is claimed is:

1. A substrate cleaning method for processing substrates by using a substrate cleaning apparatus having an indexer for receiving a cassette storing a plurality of substrates, a cleaning unit for cleaning a substrate, a particle inspecting unit for detecting a distribution of particles adhering to the substrate, and a transport unit for transporting the substrate between the indexer, the cleaning unit and the particle inspecting unit, said method comprising the steps of:
   a) cleaning a back surface of a substrate transported from said cassette to said cleaning unit;
   b) detecting a distribution of particles on the back surface of the substrate cleaned by said cleaning unit and transported to said particle inspecting unit;
   c) determining whether the back surface of the substrate is clean, based on the distribution of particles detected in said particle detecting step (b);
   d) if the substrate is determined to be unclean in said determining step (c), varying substrate cleaning conditions of said cleaning unit based on the distribution of particles detected by said particle inspecting unit;
   e) transporting the substrate determined to be unclean in said determining step (c) to said cleaning unit, cleaning the substrate again with the cleaning conditions being as varied in said cleaning condition varying step (d); and
   f) repeating steps (b), (c) and if necessary (d) and (e) until said back surface is determined to be clean in said determining step (c); and then:
   g) cleaning a front surface of said substrate using said cleaning unit;
   h) detecting a distribution of particles on the front surface of the substrate cleaned by said cleaning unit and transported to said particle inspecting unit;
   i) determining whether the front surface of the substrate is clean, based on the distribution of particles detected in said particle detecting step (h);
   j) if the substrate is determined to be unclean in said determining step (i), varying substrate cleaning conditions of said cleaning unit based on the distribution of particles detected by said particle inspecting unit;
   k) transporting the substrate determined to be unclean in said determining step (i) to said cleaning unit, cleaning the substrate again with the cleaning conditions as being as varied in said cleaning condition varying step (j);
   l) repeating steps (h), (i) and if necessary (j) and (k) until in said determining step (i) said front surface is determined to be clean;
   m) after a first substrate has been determined to be clean in step (i) after being cleaned with a final set of front and back surface cleaning conditions; then cleaning front and back surfaces of at least one additional substrate in said cleaning unit using said final set of front and back surface cleaning conditions; and
   n) repeating step (m) until all substrates in said cassette have been cleaned and determined to be clean.

2. A substrate cleaning method as defined in claim 1, a back surface cleaning step and a front surface cleaning step for cleaning a substrate with a cleaning brush, and varying at least one of a rotating speed of said cleaning brush and a pressing force of said cleaning brush applied to the substrate, based on the distribution of particles adhering to the substrate after the substrate is cleaned by said cleaning means and inspected by said particle inspecting means.

3. A substrate cleaning method as defined in claim 1, a back surface cleaning step and a front surface cleaning step for cleaning a substrate by supplying a cleaning solution under high pressure from a cleaning solution supply nozzle to the substrate, and varying at least one of a pressure and a discharge rate of the cleaning solution supplied from said cleaning solution supply nozzle, based on the distribution of particles adhering to the substrate after the substrate is cleaned by said cleaning means and inspected by said particle inspecting means.

4. A substrate cleaning method as defined in claim 1, a back surface cleaning step and a front surface cleaning step for cleaning a substrate by supplying a cleaning solution, with ultrasonic vibration applied thereto, from a cleaning solution supply nozzle to a substrate to clean the substrate, and varying at least one of a pressure and a discharge rate of the cleaning solution supplied from said cleaning solution supply nozzle, based on the distribution of particles adhering to the substrate after the substrate is cleaned by said cleaning means and inspected by said particle inspecting means.

5. A substrate cleaning method as defined in claim 1, a back surface cleaning step and a front surface cleaning step for cleaning a substrate by supplying a cleaning solution in form of spray having a liquid-gas mixture, from a cleaning solution supply nozzle to a substrate to clean the substrate, and varying at least one of a flow rate of a gas supplied to said cleaning solution supply nozzle and a flow rate of a liquid supplied to said cleaning solution supply nozzle, based on the distribution of particles adhering to the substrate after the substrate is cleaned by said cleaning means and inspected by said particle inspecting means.

* * * * *